US007199545B2

(12) United States Patent
Oleynikov et al.

(10) Patent No.: US 7,199,545 B2
(45) Date of Patent: Apr. 3, 2007

(54) ROBOT FOR SURGICAL APPLICATIONS

(75) Inventors: Dmitry Oleynikov, Omaha, NE (US); Shane Farritor, Omaha, NE (US); Adnan Hadzialic, Lincoln, NE (US); Stephen R. Platt, Lincoln, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 11/398,174

(22) Filed: Apr. 5, 2006

(65) Prior Publication Data

US 2006/0196301 A1 Sep. 7, 2006

Related U.S. Application Data

(63) Continuation of application No. 10/616,096, filed on Jul. 8, 2003, now Pat. No. 7,042,184.

(51) Int. Cl.
*B25J 5/00* (2006.01)
*A61B 1/00* (2006.01)

(52) U.S. Cl. ............................ 318/568.12; 318/568.11; 128/899; 104/138.2; 600/114; 600/102

(58) Field of Classification Search .................. 318/16, 318/568.12, 568.11; 104/138.2; 600/101, 600/114, 160, 141, 146, 102; 128/899
See application file for complete search history.

(56) References Cited

U.S. PATENT DOCUMENTS 3,870,264 A 3/1975 Robinson
4,568,311 A 2/1986 Miyaki
4,852,391 A * 8/1989 Ruch et al. .............. 73/40.5 R
5,172,639 A * 12/1992 Wiesman et al. ........ 104/138.2
5,201,325 A 4/1993 McEwen et al.
5,271,384 A 12/1993 McEwen et al.
5,284,096 A * 2/1994 Pelrine et al. ........... 104/138.2
5,304,899 A * 4/1994 Sasaki et al. ................. 318/16
5,307,447 A 4/1994 Asano et al.
5,363,935 A * 11/1994 Schempf et al. ............. 180/9.1
5,382,885 A 1/1995 Salcudean et al.
5,388,528 A * 2/1995 Pelrine et al. ................ 105/78
5,436,542 A 7/1995 Petelin et al.
5,674,030 A 10/1997 Sigel
5,728,599 A 3/1998 Rostoker et al.
5,736,821 A * 4/1998 Suyama ....................... 318/16

(Continued)

FOREIGN PATENT DOCUMENTS

JP 07306155 11/1995

(Continued)

OTHER PUBLICATIONS

Fireman, Z. et al. "Diagnosing small bowel Crohn's disease with wireless capsule endoscopy." *Gut Online*. 2003, 52:390-392. BMJ Publishing Group Ltd.

(Continued)

*Primary Examiner*—Paul Ip
(74) *Attorney, Agent, or Firm*—Dorsey & Whitney LLP

(57) ABSTRACT

The present invention provides a robot for use inside an open abdominal cavity during minimally-invasive surgery. The robot may include various sensors, imaging devices or manipulators.

21 Claims, 21 Drawing Sheets

U.S. PATENT DOCUMENTS

| | | | | |
|---|---|---|---|---|
| 5,845,646 | A | 12/1998 | Lemelson | |
| 5,878,783 | A * | 3/1999 | Smart | 138/93 |
| 6,031,371 | A | 2/2000 | Smart | |
| 6,058,323 | A | 5/2000 | Lemelson | |
| 6,107,795 | A * | 8/2000 | Smart | 324/220 |
| 6,132,368 | A | 10/2000 | Cooper | |
| 6,159,146 | A | 12/2000 | El Gazayerli | |
| 6,162,171 | A * | 12/2000 | Ng et al. | 600/141 |
| 6,286,514 | B1 | 9/2001 | Lemelson | |
| 6,293,282 | B1 | 9/2001 | Lemelson | |
| 6,309,403 | B1 * | 10/2001 | Minor et al. | 606/205 |
| 6,321,106 | B1 | 11/2001 | Lemelson | |
| 6,327,492 | B1 | 12/2001 | Lemelson | |
| 6,394,998 | B1 | 5/2002 | Wallace et al. | |
| 6,400,980 | B1 | 6/2002 | Lemelson | |
| 6,450,104 | B1 * | 9/2002 | Grant et al. | 104/138.2 |
| 6,468,203 | B2 * | 10/2002 | Belson | 600/146 |
| 6,508,413 | B2 | 1/2003 | Bauer et al. | |
| 6,512,345 | B2 * | 1/2003 | Borenstein et al. | 318/568.12 |
| 6,548,982 | B1 | 4/2003 | Papanikolopoulos et al. | |
| 6,610,007 | B2 * | 8/2003 | Belson et al. | 600/146 |
| 6,648,814 | B2 * | 11/2003 | Kim et al. | 600/114 |
| 6,661,571 | B1 | 12/2003 | Shioda et al. | |
| 6,687,571 | B1 * | 2/2004 | Byrne et al. | 700/245 |
| 6,692,485 | B1 | 2/2004 | Brock et al. | |
| 6,702,734 | B2 | 3/2004 | Kim et al. | |
| 6,714,841 | B1 | 3/2004 | Wright et al. | |
| 6,719,684 | B2 * | 4/2004 | Kim et al. | 600/101 |
| 6,728,599 | B2 | 4/2004 | Wright et al. | |
| 6,774,597 | B1 * | 8/2004 | Borenstein | 318/568.12 |
| 6,783,524 | B2 | 8/2004 | Anderson et al. | |
| 6,785,593 | B2 | 8/2004 | Wang et al. | |
| 6,799,065 | B1 | 9/2004 | Niemeyer | |
| 6,804,581 | B2 | 10/2004 | Wang et al. | |
| 6,820,653 | B1 | 11/2004 | Schempft et al. | |
| 6,824,508 | B2 | 11/2004 | Kim et al. | |
| 6,824,510 | B2 | 11/2004 | Kim et al. | |
| 6,832,988 | B2 | 12/2004 | Sproul | |
| 6,860,346 | B2 | 3/2005 | Burt et al. | |
| 6,870,343 | B2 | 3/2005 | Borenstein et al. | |
| 6,917,176 | B2 | 7/2005 | Schempf et al. | |
| 6,991,627 | B2 | 1/2006 | Madhani et al. | |
| 7,042,184 | B2 | 5/2006 | Oleynikov et al. | |
| 7,126,303 | B2 | 10/2006 | Farritor et al. | |
| 2001/0018591 | A1 | 8/2001 | Brock et al. | |
| 2002/0003173 | A1 | 1/2002 | Bauer et al. | |
| 2002/0091374 | A1 | 7/2002 | Cooper | |
| 2002/0103417 | A1 | 8/2002 | Gazdzinski | |
| 2002/0111535 | A1 | 8/2002 | Kim et al. | |
| 2002/0120254 | A1 | 8/2002 | Julian et al. | |
| 2002/0140392 | A1 | 10/2002 | Borenstein et al. | |
| 2002/0156347 | A1 * | 10/2002 | Kim et al. | 600/160 |
| 2002/0190682 | A1 * | 12/2002 | Schempf et al. | 318/568.11 |
| 2003/0045888 | A1 | 3/2003 | Brock et al. | |
| 2003/0089267 | A1 * | 5/2003 | Ghorbel et al. | 104/138.1 |
| 2003/0092964 | A1 * | 5/2003 | Kim et al. | 600/101 |
| 2003/0167000 | A1 | 9/2003 | Mullick et al. | |
| 2003/0172871 | A1 | 9/2003 | Scherer | |
| 2003/0179308 | A1 | 9/2003 | Zamorano et al. | |
| 2003/0230372 | A1 * | 12/2003 | Schmidt | 156/64 |
| 2004/0024311 | A1 | 2/2004 | Quaid | |
| 2004/0034282 | A1 | 2/2004 | Quaid | |
| 2004/0034283 | A1 | 2/2004 | Quaid | |
| 2004/0034302 | A1 | 2/2004 | Abovitz et al. | |
| 2004/0070822 | A1 | 4/2004 | Shioda et al. | |
| 2004/0099175 | A1 | 5/2004 | Perrot et al. | |
| 2004/0106916 | A1 | 6/2004 | Quaid et al. | |
| 2004/0111113 | A1 | 6/2004 | Nakamura et al. | |
| 2004/0140786 | A1 * | 7/2004 | Borenstein | 318/568.12 |
| 2004/0173116 | A1 * | 9/2004 | Ghorbel et al. | 104/138.2 |
| 2004/0254680 | A1 | 12/2004 | Sunaoshi | |
| 2005/0029978 | A1 | 2/2005 | Oleyikov et al. | |
| 2006/0119304 | A1 | 6/2006 | Farritor et al. | |

FOREIGN PATENT DOCUMENTS

| | | |
|---|---|---|
| WO | WO 02/082979 | 10/2002 |

OTHER PUBLICATIONS

Abbou, Clement-Claude et al. "Laparoscopic Radical Prostatectomy with a Remote Controlled Robot." *The Journal of Urology*. Jun. 2001, 165: 1964-1966.

Fraulob, S. et al. "Miniature assistance module for robot-assisted heart surgery." *Biomed. Tech.* 2002, 47 Suppl. 1, Pt. 1: 12-5.

Guber, A. E. et al. "Miniaturized Instrument Systems for Minimally Invasive Diagnosis and Therapy." *Biomedizinische Technik*. 2002, Band 47, Erganzungsband 1: 198-201.

Thomann, G. et al. "The Design of a new type of Micro Robot for the Intestinal Inspection." *Proceedings of the 2002 IEEE/RSJ Intl. Conference on Intelligent Robots and Systems EPFL*. Oct. 2002: 1385-1390.

Guo, Shuxiang et al. "Fish-like Underwater Microrobot with 3 DOF." *Proceedings of the 2002 IEEE International Conference on Robotics & Automation*. May 2002: 738-743.

Fukuda, Toshio et al. "Mechanism and Swimming Experiment of Micro Mobile Robot in Water." *Proceedings of the 1994 IEEE International Conference on Robotics and Automation*. 1994: 814-819.

Guo, Shuxiang et al. "Micro Active Guide Wire Catheter System-Characteristic Evaluation, Electrical Model and Operability Evaluation of Micro Active Catheter," *Proceedings of the 1996 IEEE International Conference on Robotics and Automation*. Apr. 1996: 2226-2231.

Yu, Sun et al. "Microrobotic Cell Injection." *Proceedings of the 2001 IEEE International Conference on Robotics & Automation*. May 2001: 620-625.

Ruurda, JP et al. "Robot-assisted surgical systems: a new era in laparoscopic surgery." *Ann. R. Coll. Surg. Engl.* 2002, 84: 223-226.

Menciassi, A. et al. "Robotic Solutions and Mechanisms for a Semi-Autonomous Endoscope." *Proceedings of the 2002 IEEE/RSJ Intl. Conference on Intelligent Robots and Systems EPFL*. Oct. 2002: 1379-1384.

Ishiyama, K. et al. "Spiral-type Micro-machine for Medical Applications." *2000 International Symposium on Micromechatronics and Human Science*. 2000: 65-69.

Fearing, R. S. et al. "Wing Transmission for a Micromechanical Flying Insect." *Proceedings of the 2000 IEEE International Conference on Robotics & Automation*. Apr. 2000: 1509-1516.

Mei, Tao et al. "Wireless Drive and Control of a Swimming Microrobot." *Proceedings of the 2002 IEEE International Conference on Robotics & Automation*. May 2002: 1131-1136.

Marcia Yu, BSN, RN, "M2ATM Capsule Endoscopy A Breakthrough Diagnostic Tool for Small Intestine Imaging," vol. 25, No. 1, *Gastroenterology Nursing*, pp. 24-27 2001.

Andrew Miller, D. et al., "In-Vivo Steroscopic Imaging System with 5 Degrees-of-Freedom for Minimal Access Surgery," Dept. of Computer Science and Dept. of Surgery, Columbia University, New York, NY, p. 7. No Date.

Strong, et al. "Efficacy of Novel Robotic Camera vs a Standard Laparoscopic Camera," *Surgical Innovation*, vol. 12, No. 4, Dec. 2005, Westminster Publications, Inc., pp. 315-318.

Worn et al., "Espirit Project No. 33915: Miniaturized Robot for Micro Manipulation (Miniman) ", Nov. 1998, http://www.ipr.lra.uka.de/-microrobot/miniman/.

Meron, G., "The development of the swallowable video capsule (M2a)," Gastrointestinal Endoscopy 2000, 52, 6;817-819.

Phee et al., " Development of Microrobotic Devices For Locomotion in the Human Gastrointesinal Tract ", *International conference on Computational Intelligence*. No Date.

Breda et al., " Future developments and perspectives In Lacroscopy ", *Eur. Urology*, 2001, 40, 1: 84-91.

* cited by examiner

ROBOT FOR SURGICAL APPLICATIONS

INTRODUCTION

This application is a continuation of U.S. patent application Ser. No. 10/616,096 filed Jul. 8, 2003 now U.S. Pat. No. 7,042,184, incorporated herein by reference in its entirety.

BACKGROUND OF THE INVENTION

Interest in micro-robotics has increased rapidly in recent years. This is due mainly to technology development in the fields of microelectronics, micromachining, and microactuation. Currently, it is possible to build and test miniature systems that include numerous features, including sensors, actuators, and embedded control subsystems. The trend toward miniaturization is seen not only in industrial applications, but in medical applications as well.

There are many industrial applications for micro-robots. Micro-robots are suitable for work in small and inaccessible places; for example, in dismantling and reassembling factory pipelines, inspection of small environments, measuring various parameters, miniature manipulation, repairs, micromachining, complex molecular and atomic operations, and precision tooling, grasping, transport, and positioning with nanoscale motion resolution. Micro-robots that mimic insects have been developed, though currently such microrobots are of limited use due to their size and low-level agility (see Fearing, et al., *Proceedings of the* 2000 *IEEE International Conference on Robotics and Automation*, p. 1509–16 (2000)). Mobile micro-robots, such as swimming robots, are used for inspection and repair of thin pipes. Most of micro-robots concentrate on specific tasks and require high voltages, which means they cannot be wireless. Microrobots with small power requirements generally are suitable only for simple tasks, like moving forward and backward.

There are an increasing number of medical applications for micro-robots, such as in biological cell manipulation, blood-flow measurement, microsurgery of blood vessels and endoscopic surgery (a minimally invasive surgery). However, micro-robots have not been applied in laparoscopic or other minimally invasive surgery to date. Laparoscopic surgery avoids the trauma traditionally inflicted in gaining access to abdominal organs by using long, rigid instruments and cameras inserted into the body through small incisions. While minimally invasive surgical procedures reduce patient trauma, pain, recovery time, and hospital costs, there are several drawbacks to the technique. For example, there are regions of the patient that are inaccessible with current methods, and there is a lack of tactile feedback and limited dexterity and perception.

One micro-robot used currently in medical applications is a semi-autonomous endoscope device used during colonoscopy. The main advantage of this device is that the procedure generates only "internal" forces, unlike standard colonoscopy where the physician must provide high external forces to overcome acute intestinal bends. Two propulsion mechanisms have been proposed. One is based on "inchworm" locomotion, while the other uses "sliding clamper" locomotion (Menciassi, et al., *Proceedings of the* 2002 *IEEE/RSJ International Conference on Intelligent Robots, EPFL*, p. 1379–84 (2002)).

Also, a miniature disposable imaging capsule has been developed. The capsule is swallowed by the patient and, with the natural movement of bowel, it moves through the gastrointestinal tract, and is passed naturally out of the body. The capsule transmits information (such as imaging information) to a receiver worn by the patient, which is later processed on a computer. The capsule consists of optical dome, lens holder, lens, illuminating LEDs, CMOS imager, battery, transmitter, and antenna. This device is used for colonoscopy. A similar device that is radio-controlled allowing for limited movement has been tested by researcher Annette Fritscher-Ravens at the University of London.

A device similar to that of Menciassi, et al., which is electro-pneumatically driven, has been developed. The advantage of this micro-robot is that it minimizes the contact between the colonoscope and the interior boundary of the colon, which makes the progression of colonoscope easier. The design uses three metal bellows disposed 120 degrees apart, while the position in the intestine is driven by three sensors positioned on a superior plate (Thoman, et al., *Proceedings of the* 2002 *IEEE/RSJ International Conference on Intelligent Robots, EPFL*, p. 1385–90 (2002)).

A Japanese company has developed miniature prototypes of endoscopic tools. One is an autonomous endoscope that can move through a patient's veins. Another prototype is catheter mounted with a tactile sensor to examine tumors for malignancy.

A prototype of a micro-catheter with active guide wire has been proposed. The active guide wires are composed of hollow cable, and have two bending degrees of freedom (DOF) using an ionic conduction polymer film (ICPF) actuator on the front end. Use of an ICPF actuator provides the catheter with flexibility, good response, low voltage and safety (Guo, et al., *Proceedings of the* 1996 *IEEE International Conference on Robots and Automation*, (3):2226–31 (1996)). A shape memory alloy (SMA) actuator has been proposed as well, but has some disadvantages, such as cooling, leaking electric current, and response delay (Fukuda, et al., *Proceedings of the* 1994 *IEEE International Conference on Robotics and Automation*, p. 418–23 (1994)).

In addition, use of an ICPF actuator has been used in a fish-like robot that has three degrees of freedom and has been proposed for use in procedures involving aqueous media such as blood. The actuator is used as a propulsion tail fin and a buoyancy adjuster. The moving motion (forward, right, or left) is manipulated by changing the frequency of the applied voltage. The device is 45 mm long, 10 mm wide, and 4 mm thick, and may be used in microsurgery of blood vessels (Guo, et al., *Proceedings of the* 2002 *IEEE International Conference on Robotics and Automation*, p. 738–43 (2002)). See also Mei, et al., *Proceedings of the* 2002 *International Conference on Robotics and Automation*, p. 1131–36 (2002).

A spiral-type magnetic swimming micro-machine has been developed. This device is driven by a rotating magnetic field, which implies that the system is wireless and does not require batteries of any kind. The micro-machine is composed of a cylindrical NdFeB magnet, ceramic pipes, and a spiral blade. The prototype length is 15 mm with a 1.2 mm diameter. It was shown that the device is suitable for miniaturization. The swimming direction of the machine can be controlled by changing the direction of the rotational magnetic field, while the velocity can be adjusted by changing the frequency of the rotating magnetic field. Tests have shown that in addition to running in a blood-like environment, the micro-machine has potential use in human organs (Ishiyama, et al., *International Symposium on Micromechatronics and Human Science*, p. 65–69 (2000

Micro-robots are being used for performing automatic DNA injection autonomously and semi-autonomously through a hybrid visual serving control scheme. The system is composed of an injection unit, an imaging unit, a vacuum unit, a microfabricated unit, and a software unit. A high precision, three DOF micro-robot is a part of the injection unit. The micro-robot is used to precisely place the injection pipette. In addition to being able to perform pronuclei DNA injection, the system is suitable for performing intracytoplasmic injection (Yu and Nelson, *Proceedings of the* 2001 *IEEE International Conference on Robotics and Automation*, p. 620–25 (12001)).

However, there is a need in the art for robots that allow one to treat pathological organs while preserving healthy tissues, yet provide dexterity enhancement, enhanced perception, improved access, and remote treatment capabilities. The present invention fulfills this need in the art.

SUMMARY OF THE INVENTION

The robot of the present invention provides a mobile robotic system to be used inside an open abdominal cavity in minimally invasive surgery, particularly laparoscopy. The robot according to the present invention may comprise various sensors including but not limited to, in various embodiments, sensors to measure temperature, blood or other fluids in tissue, humidity, pressure and/or pH. In addition, the robot comprises one or more transceivers and imaging capability. In addition, in some embodiments, the robot of the present invention may include one or more manipulators. Certain embodiments of the invention are adapted to fit through standard laparoscopic tools for use in the abdomen during laparoscopic surgery. The invention provides both wired and wireless embodiments.

Thus, the present invention provides robots for performing minimally-invasive surgery inside open abdominal cavities, including human bodies, where the robots comprise a body; mobilization means such as wheels or tracks for moving the robot; controller means for remotely controlling the mobilization means; an actuator; a power supply; and a manipulator, one or more sensor devices or a manipulator and one or more sensor devices. The robot of the present invention may, in various embodiments, take on many different configurations, such as cylindrical or spherical shapes, or, alternatively, a shape such as that of a small vehicle. The robot of the present invention in one embodiment is tethered or wired, and in another embodiment, it is wireless. When the robot is wireless, an internal power supply is used, and the robot further comprises a receiver and a transmitter. The robot may use any type of compatible actuator. Also, another embodiment of the invention comprises a body, a sensor, mobilization means to move the sensor, a controller to remotely control the mobilization means, an actuator and a power supply.

The sensor devices of the present invention include those that sense pH, temperature, gasses, fluids such as blood, electrical potential, heart rate, fluid composition, respiration rate or humidity. In addition, the sensor may be a camera or other imaging device. The manipulator of the present invention may comprise an arm or other means for positioning the manipulator element. Another embodiment of the present invention provides use of the robot of the present invention inside the abdominal cavity in minimally-invasive surgical applications.

BRIEF DESCRIPTION OF THE DRAWINGS

FIG. 19 shows two circuits used in one embodiment of a manipulator arm of the present invention.

FIG. 23A shows the results for the motor for link 1, FIG. 23B shows the results for the motor for link 2, and FIG. 23C shows the results for the motor for link 3.

FIG. 24A shows the results for the motor for link 1, FIG. 24B shows the results for the motor for link 2, and FIG. 24C shows the results for the motor for link 3.

FIG. 26A shows the results for link 1.

FIG. 27A shows the results for link 1, FIG. 27B shows the results for link 2, and FIG. 27C shows the results for link 3.

FIG. 29 shows the response of the systems for links 1 and 3 with compensators.

DETAILED DESCRIPTION OF THE INVENTION

Figure 1:
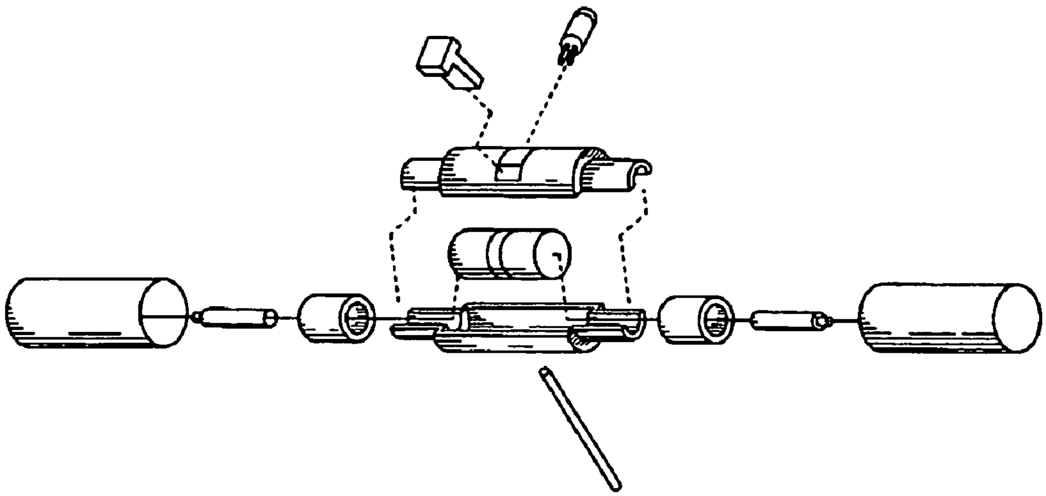
FIG. 1 is an exploded view of the initial prototype of the mobile robot.

A more particular description of the invention, briefly summarized above, may be had by reference to the embodiments of the invention described in the present specification and illustrated in the appended drawings. It is to be noted, however, that the specification and appended drawings illustrate only certain embodiments of this invention and are, therefore, not to be considered limiting of its scope. The invention may admit to equally effective embodiments.

Reference will now be made in detail to exemplary embodiments of the invention. While the invention will be described in conjunction with these embodiments, it is to be understood that the described embodiments are not intended to limit the invention solely and specifically to only those embodiments. On the contrary, the invention is intended to cover alternatives, modifications, and equivalents that may be included within the spirit and scope of the invention as defined by the attached claims.

The increased use of laparoscopy has led to a dramatic shift in surgical methods and improvements in patient care. Laparoscopic surgery avoids the trauma traditionally inflicted in gaining access to the abdominal organs by using long, rigid instruments and cameras inserted into the abdominal cavity through small incisions. Maneuvering space for the tools used is created by insufflating $CO_2$ to lift the abdominal wall away from the organs. The reduced surgical invasiveness in laparoscopic surgery results in fewer complications and a more rapid recovery for the patient. The adoption of laparoscopic techniques has been driven by technological advances such as imaging systems and, recently, robots. Surgical laparoscopic robots currently are used to maneuver and position instruments with high precision and allow micro-scale tasks otherwise not possible. Despite these successes, however, laparoscopy remains constrained in application due to the loss of sensory feedback, limited imaging and the reduced mobility and dexterity associated with current approaches.

The present invention facilitates the application of laparoscopy and other minimally invasive surgical techniques to a much wider range of procedures by providing semi-autonomous and autonomous remotely controlled robots that are used inside cavities, especially human bodies. The present invention provides robotic in vivo wired and wireless manipulator, imaging and sensor devices that are implanted in the area to be treated, for example, the abdomen. The devices overcome the limitations associated with current generation laparoscopic cameras and tools, providing the surgical team a view of the surgical field from multiple angles, in vivo patient monitoring capability and in vivo manipulator dexterity.

One embodiment of the robot of the present invention provides one or more sensors, including one or more types of imaging capabilities, which increase the view of the abdominal cavity for the surgical team. Current laparoscopes use rigid, single view cameras inserted through a small incision. The camera has a limited field of view and its motion is highly constrained. To obtain a new perspective using this prior art technique often requires the removal and reinsertion of the camera through another incision thereby increasing patient risk. Instead, the present invention provides one or more robots inside an abdominal cavity to deliver additional cavity images that improve the surgeon's geometric understanding of the surgical area.

In addition, in yet another embodiment of the present invention other sensors are provided, such as those that measure, for example, temperature, pressure, presence of various gases and/or humidity or other parameters. Current minimally invasive surgical techniques, due to their remote nature, decrease the surgeon's ability to sense the surgical environment. The sensor-equipped robot according to embodiments of the present invention restores the surgeon's ability to perform more complex procedures and more accurately monitor patient health.

In yet another embodiment of the present invention, the robot comprises a manipulator that assists the surgeon in tasks requiring high dexterity. In current techniques, movement is restricted, as passing the rigid laparoscopic tool through a small incision restricts movement and positioning of the tool tip. A robot manipulator inside a cavity, as provided by the present invention, is not subject to the same constraints.

The present invention is novel as it is the first application of in vivo mobile robots in minimally invasive surgery, such as laparoscopy. Previous integration of surgery and robots has involved large robots on the outside of the patient, such as those sold by Intuitive Surgical, Inc. (Sunnyvale, Calif.) and described by Ruurda, et al., *Ann. R. Coll. Surg. Engl.,* 84:223–226 (2002). The use of robots in vivo represents a fundamental paradigm shift in robot-assisted surgery.

The present invention provides robotic wired and wireless manipulator, imaging and sensor devices for use in vivo. The robots may take on any configuration and be equipped with any number of sensors, manipulators or imaging devices. There are hundreds of different components known in the art of robotics that can be used in the construction of the robots of the present invention; for example, there are hundreds controllers, motors, power supplies, wheels, bodies, receivers, transmitters, cameras, manipulators, and sensing devices that can be used in various combinations to construct robots according to the present invention.

In the examples herein, the controllers used for the mobile robot prototypes were constructed from scratch, whereas for the manipulator, a motion control card from Motion Engineering Incorporated (MEI) was used. Accordingly, controllers may be purchased from commercial sources, constructed de novo, or commercially available controllers may be customized to control the robotic components of the present invention. One skilled in the art would be able to select a controller appropriate for the robot or manipulators according to the present invention.

Likewise, actuators useful in the present invention may be of many types. The mobile robot described herein used a Nakamishi brushless direct current motor that has been used commonly in robotic and other applications. These motors require external communication, generally performed by a circuit supplied by the manufacturer. The manipulator described in the Example herein used a permanent magnet DC motor made by MicroMo™. Again, permanent magnet DC motors are commonly used devices. However, other devices would be useful in alternative embodiments of the present invention, including shape memory alloys, piezo-electric-based actuators, pneumatic motors, or hydraulic motors, or the like. Pneumatic and hydraulic motors are efficient, but the pump generally must be external to the robot. Thus, such motors may be useful in a tethered or wired embodiment of the present invention, but not in the wireless embodiment of the present invention.

When selecting a power supply, both the mobile robot and the manipulator of the present invention used external power supplied in a tethered configuration, but in an alternative embodiment, could have been powered by batteries. Versions of the robot and/or manipulator of the present invention may use alkaline, lithium, nickel-cadmium, or any other type of battery known in the art. Alternatively, magnetic induction is another possible source of power, as is piezoelectrics. In addition, one of skill in the art could adapt other power sources such as nuclear, fluid dynamic, solar or the like to power the robots of the present invention.

A distinctive feature of the present invention is its mobility. The embodiment detailed in the Example herein used treaded wheels for mobility; however, the present invention also contemplates use of alternative methods of mobility such as walking robots, treads or tracks (such as used in tanks), hybrid devices that include combinations of both wheels and legs, inchworm or snake configurations that move by contorting the body of the robot, and the like. The wheels used on the mobile robot described herein were made out of aluminum and rubber; however, virtually any material may be used to construct the wheel or other mobility-creating element as long as sufficient traction is obtained. The wheel shape used herein was a round, tubular-type treaded configuration; however, again, virtually any configuration could be employed including round, square, spherical, triangular, as long as sufficient traction is obtained and trauma to the areas traversed are minimized.

Receivers and transmitters useful in the present invention are many, such as those used on remote locks, such as for cars and other vehicles, other remote controls, and receiver and transmitter elements used in cell phones. Essentially, the input to the robot would be user command signals to the device, for example, to move various components such as the device itself, or for positioning the camera, sensor components or manipulator. The output from the robot would be primarily data from the video or sensors.

The mobile robot of the present invention was cylinder-shaped so as to be compatible with laparoscopic tools known currently in the art. However, as with the other components, the body configuration of robots according to the present invention is not limited to the mobile robot presented in the Example herein. Indeed, the only constraints on the shape of the body of the robot in various embodiments are that the body be able to incorporate the imaging, sensor and/or manipulator components required; not affect adversely the traction required; or cause trauma to the areas of the cavity traversed.

The cameras, imaging devices and sensors of the present invention can be any known in the art that are compatible with the various designs and configurations of the invention. For example, small cameras are becoming common in devices such as cellular phones, and these cameras may be used in the present invention. In addition, imaging devices have been used in the endoscopic devices described earlier herein, and those devices may be used as well. Sensor devices can be any of those used in the art compatible with the small size of the robot. For example, various sensors for temperature, pH, $CO_2$, other gasses, electrical potential, heart rate, respiration, humidity and the like are known and are commercially available. As with the body configuration, any camera, imaging device or sensor may be used as long as it does not affect adversely traction or the safety of the patient.

Finally, manipulators according to the present invention can be, like the prototype presented in the Example herein, constructed de novo; alternatively, manipulators of the present invention may be purchased from commercial sources. The manipulators according to the present invention are small compared to traditional manipulators, and my come in any shape as long as it does not adversely affect traction of the device or the safety of the patient, and as long as it is able to accomplish the tasks required in the surgical manipulation.

The invention is described in greater detail by the following non-limiting examples.

EXAMPLE 1

Mobile Mini Robot

The constraints placed on the size of the robot according to the present invention were factors in determining the size and shape of the initial prototype of the embodiment described herein. The mobile robot was constructed to be cylindrical in shape, with the treaded wheels of the mobile robot covering a substantial portion of the surface area of the body. The robot's diameter was designed to be less than 15 mm so as to be able to, in this embodiment, fit through a port in a tool that is currently used in laparoscopic surgical techniques.

The size and function of this robot dictated also the use of very small electric motors. The first motors tested were motors that are used to vibrate pagers and mobile phones; however, these motors were found to be inadequate to supply the torque needed to move the robot. A suitable motor was selected. The electronics selected initially consisted of a modified control chip for the brushless motors that were selected. After control for the motors was established, the motors were wired to a game controller consisting of two joysticks. Each wheel on the robot was controlled by a separate joystick.

The first test of the robot was to use it to perform surgery in a pig. From this test it was found that there was insufficient traction to move the robot on the wet surfaces inside the body. This test resulted in a search for alternative wheel materials and wheel configuration. A second set of testing was then done in the lab, focusing on the incline that the robot was capable of climbing. Friction tests were done to find the frictional forces between the current aluminum wheels and several different surfaces.

The most critical and unusual aspect of this embodiment of the robot is its size. The size limitation is what distinguishes this robot design from any other robot known in the art and drove the initial design constraints. Since the mobile robot was designed, in this embodiment, to be inserted through a standard 15 mm medical port, an overall cylindrical configuration was determined to maximize the allowable space. Therefore, as a starting point, the mobile robot was roughly cylindrical with a 15 mm outside diameter. As the internal components become better defined through testing, the outside diameter could be reduced if needed. The overall length of the device was less of a priority. Smaller was assumed to be better, but lacking a hard constraint, the length was left initially undefined.

After physical size, the next priority was that the device be easy to control by an operator, most likely a surgeon. The robot, for example, must be able to move about the abdominal cavity of a human being and transmit real-time video without being a distraction to the surgeon.

The robot was designed to be able to move forward, backward, and turn in the smallest circle possible. Because of the cylindrical configuration of the device, a two-wheeled vehicle was chosen. In forward or backward motion, both wheels rotate at the same speed. To turn, this embodiment of the two-wheel mobile robot used skid steering to turn like a tank, the motors rotating at different speeds and/or directions. In this embodiment, where each wheel must be controlled individually, each wheel was given its own motor. However, two wheels are not enough to achieve the required motion. Since the wheels are coaxial, their rotation alone will not translate the robot across a surface without some non-rotating element in the robot. Because of this, the robot had to have some sort of "tail"; something that would contact the surface and convert rotational motion into translational motion. The tail was mounted to the main body of the robot between the wheels.

Throughout the operation of this embodiment of the robot, it was desired that the operator would be provided with real-time video from an on-board camera or imaging device. For such a camera or imaging device to be useful, it would need to have adequate resolution, field-of-view and lighting to show details important to the operator. A square 7 mm camera was chosen that met the video requirements and would fit within the robot body. To assure adequate lighting, an LED was chosen to provide a constant (but potentially variable) source of illumination for the camera.

The camera's view must be steady while the robot moves so that situational awareness is maintained and the operator does not get lost within the body. In some embodiments, the camera points in the same direction relative to the robot, and the operator steers the robot to change the view location or perspective. In other embodiments, the camera position can be varied relative to the robot as needed by the operator. Since the center section of the robot body is limited to pure translation by the tail, mounting both the camera and LED onto the main body of the robot was the logical choice for this embodiment.

In some embodiments, the mobile robot is completely wireless and self-contained. Wiring from outside in some situations might limit the usefulness of the device, as well as reduce its mobility. A wireless embodiment of the robot of the present invention must carry its own power source to operate the motors and the camera. Such a power source may take the form, for example, of very small batteries. In addition, a wireless embodiment requires that the motors include a wireless receiver to receive commands from the operator.

Another obvious consideration in the design and operation of the robot was that the robot be safe to the patient. Components were selected that did not have sharp edges. Additionally, excessive movement optimally should be avoided. Moreover, biocompatible materials had to be selected, and, in addition, the materials had to be easy to sterilize. Further, the materials comprising the robot had to be sturdy enough so that the materials would not break inside the patient.

The mobile robot of the present invention is required to traverse a very unusual and irregular surface. The robot is required to drive across many different internal organs such as the liver, stomach, intestines, each of which has different surface properties. Some of these organs are soft and pliant, with a slippery exterior. Traction was an initial concern for the mobile robot. Moreover, the robot had to be designed such that it would not become high-centered on the tail or on the non-rotating center section. The initial robot concept countered this problem by minimizing the center area that contacted the organ surfaces.

Even with full contact upon the wheels, the robot had to overcome difficulties with the surfaces. For example, some of the organs are so soft that the robot tends to sink far below the original surface, placing it inside a deep valley or pouch out of which the robot must climb. In addition, each wheel had to be able to produce enough shear torque against the internal organs to move as required while not damaging the organs.

Based on the criteria described, an initial concept was created using a UniGraphics® solid modeling and component assembly. The main body of the initial device was made up of two nearly identical halves. The camera and LED were mounted to the top half, while the tail extended from the bottom half. The central space within the body housed two batteries and the electronic components required to control the motors and transmit the video signal. The motors were held in the slots at each end of the body. The wheels were designed to be as long as possible to minimize surface contact with the center section. Nylon bushings were used to support the inside diameter of the wheels and prevent wobble. The bushings were a light press fit with the body halves and had a smooth running fit with the wheels. The wheels had a line-to-line fit with the motor shafts.

To assemble the robot, the LED and camera were attached to the top half of the body. Next, the batteries, motors, tail and other electronic components were installed into the bottom half of the body. The two body halves were brought together and a nylon bushing was pressed over each end. The motors and batteries were held tightly within the body. Finally, the wheels were pressed onto the motor shafts.

Due to the very small size and relative complexity of the main body, machining appeared to be an unlikely method of fabrication. The only remaining inexpensive, rapid prototyping method was stereolithography. The wheels were to be turned from a solid aluminum bar. Any number of flexible materials could be used for the tail. An exploded perspective of the initial prototype is shown in FIG. 1.

Figure 2:
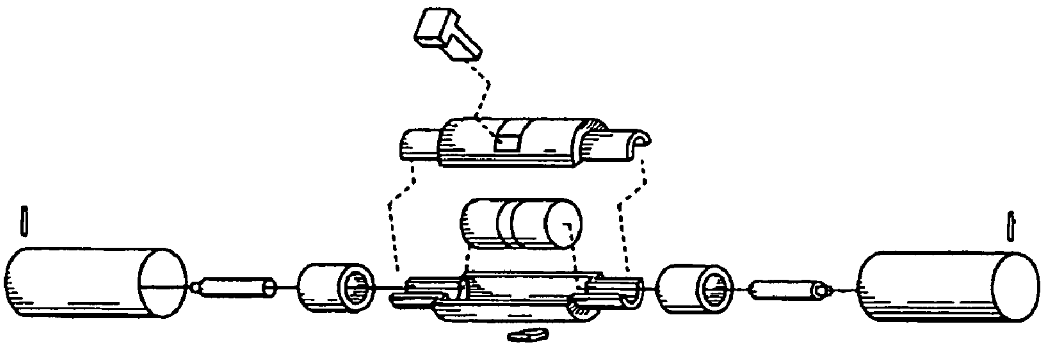
FIG. 2 is an exploded view of the second prototype of the mobile robot.

An exploded perspective of the second version of the mobile robot is shown in FIG. 2. The primary changes are the addition of wheel set screws and a flattened tail. In addition, the LED was removed as the purpose of the initial prototypes was to maximize mobility and maneuverability. Also, new batteries were found with smaller outside diameters. This was important because the battery size-determined the outside diameter of the main body center section. Reducing the body size made the wheels easier to fabricate. The new, smaller batteries allowed the inboard wheel thickness to change from 0.5 mm to a more reasonable 1.5 mm.

Figure 3:
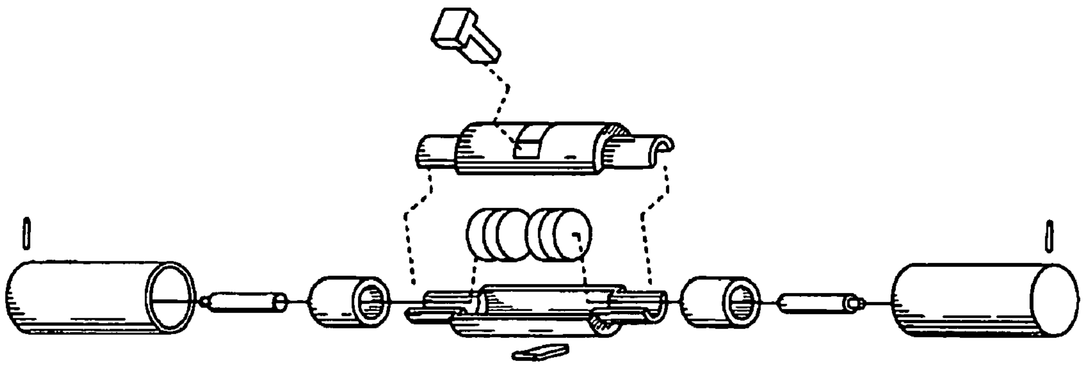
FIG. 3 is an exploded view of the third prototype of the mobile robot.

An exploded perspective of the third version of the mobile robot is shown in FIG. 3. The primary changes were that the two batteries were replaced with four smaller batteries and reduced diameters on the wheel and main body. The batteries selected were Energizer™ 309 miniature silver oxide batteries. They have a nominal voltage of 1.55 V and each have a capacity of 70 mAh. They have a diameter of 7.9 mm and a height of 5.4 mm.

Figure 4:
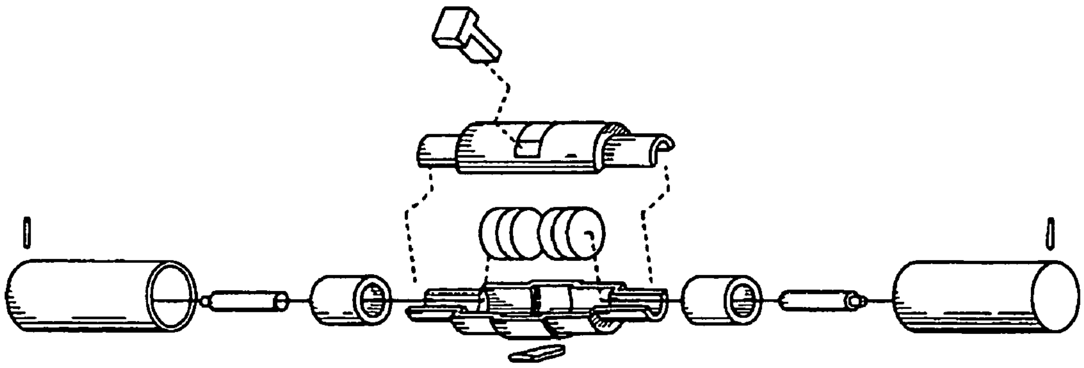
FIG. 4 is an exploded view of the fourth prototype of the mobile robot.

Version four of the mobile robot is shown in FIG. 4. The primary changes were the enlarging of the center section from ø10.4 mm to ø13 mm and the addition of 3 mm wire channels. Since the walls of main body were very thin and stereolithography can make very complex shapes, a 0.5 mm radius was also added to all interior angles.

Figure 5:
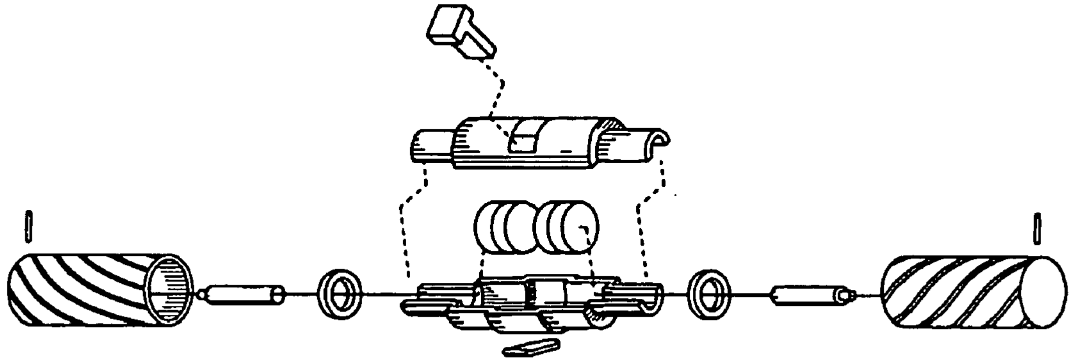
FIG. 5 is an exploded view of the fifth prototype of the mobile robot.

Upon review of version four, two final changes were made. First, the nylon bushing was reduced from 8 mm to 1 mm wide as it was determined that a long bushing would make a line of contact with the inner wheel diameter. If that happened, the motor shaft would be over-constrained and subject to potentially high loads. Reducing the bushing width ensured that its contact with the wheel bore would be closer to a single point and therefore allow the wheel to adjust to misalignment between the motor shaft and the bushing. The second change was to add a surface texture to the wheel outside diameter. An array of 6 milled spirals was planned for each wheel. Version five of the mobile robot is shown in FIG. 5. The primary changes are the addition of milled spirals to the wheels and a much thinner bushing.

There were several factors that had to be taken into consideration when selecting which motors should be used for the mobile robot. These factors included the size of the motor and the torque that the motor could provide for the movement of the robot. The size of the motors was limited by the overall size and shape of the mobile robot. The mobile robot design in this embodiment had a small cylindrical shaped robot with the wheels covering most of the robot body. The robot was to have a maximum diameter of 15 mm and as short of a length as possible, optimally, less than 90 mm.

For the robot to meet the diameter restraint, the motor that was chosen had to have a diameter of less than 10 mm so that the motor would fit easily into the body. To meet the goal of a body length of less than 90 mm, a motor that was shorter than 30 mm was selected to ensure that there would be room the for batteries and electronics.

Figure 6:
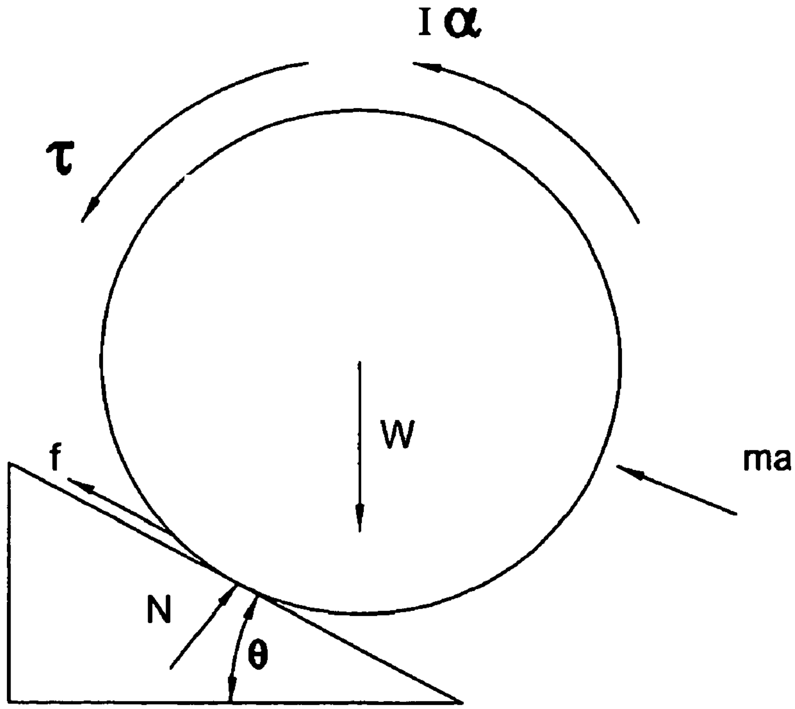
FIG. 6 is a free body diagram of the mobile robot sitting motionless on a slope.

The next step in choosing a motor was to determine how much torque would be needed to move the robot. To calculate the needed torque, a free-body diagram of the robot sitting motionless on a slope was used to calculate the torque required to keep the robot stationary on the slope. This calculation would be the stall torque that the motor would need (provided that the friction of the surface was enough to prevent the wheels from slipping). The free-body diagram is shown below in FIG. 6.

From this free-body diagram the following equations were written:

$$(W\sin\theta)r=(ma)+I\alpha+\tau$$

$$W\sin\theta-f=ma$$

$$W\cos\theta=N$$

This results in the following:

$$\tau=(W\sin\theta)r$$

where

W is the weight of the cylinder,

θis the angle of the slope, r is the radius of the cylinder, m is the mass of the cylinder, a is the acceleration of the cylinder, I is the moment of inertia of the cylinder, α is the angular acceleration of the cylinder, τ is the torque of the motor, f is the friction between the cylinder and slope, N is the normal force.

The robot was modeled as a solid aluminum cylinder 15 mm in diameter and 76 mm long. A solid aluminum cylinder of this size would have a mass of 36.4 g and a moment of inertia of 1.02 [kg–$m^2$]. The resulting calculations show that for the robot to hold its position on a slope of θ degrees a torque, τ, is needed (Table 1).

TABLE 1

Slope Angle and Required Torque

| θ | τ |
|---|---|
| 0 | 0.00 mN-m |
| 15 | 0.69 mN-m |
| 30 | 1.34 mN-m |
| 45 | 1.89 mN-m |
| 60 | 2.32 mN-m |
| 75 | 2.58 mN-m |

After determining what torque was required to move the robot, a motor and a gearhead were selected that would reduce the speed and increase the torque output from the motor. The first choice in motors for the prototypes was motors that were inexpensive and could be obtained from a commercial source. Two motors that were inexpensive and readily available were tested to determine if they met the torque requirements. The first motor was a 6 mm diameter pager motor and the second was a 6 mm ZipZap motor (blue motor). Tests determined the stall torque of the motor per volt input.

For the test, a bar was placed on the motor shaft and a voltage was applied to the motor. The angle at which the bar stalled was then measured for each applied voltage. The torque that was present on the motor shaft was calculated and plotted versus the voltage, and a linear fit was used to determine the stall torque/volt of the motor. The results of the test are shown in Table 2.

TABLE 2

Motor Torques

| 6 mm Pager Motor | | | | ZipZap Motor (Light Blue) | | | |
|---|---|---|---|---|---|---|---|
| Voltage [V] | Angle [Degrees] | Torque [mNm] | [mNm]/[V] | Voltage [V] | Angle [Degrees] | Torque [mNm] | [mNm]/[V] |
| 0.5 | 5.0 | 0.02 | 0.043 | — | — | — | — |
| 1.0 | 8.5 | 0.04 | 0.037 | 1.0 | 3.5 | 0.02 | 0.015 |
| 1.5 | 12.0 | 0.05 | 0.035 | 1.5 | 6.0 | 0.03 | 0.017 |
| 2.0 | 16.0 | 0.07 | 0.034 | 2.0 | 8.5 | 0.04 | 0.018 |
| 2.5 | 18.5 | 0.08 | 0.032 | 2.5 | 10.5 | 0.05 | 0.018 |
| 3.0 | 21.5 | 0.09 | 0.030 | 3.0 | 12.0 | 0.05 | 0.017 |
| | | Linear Fit | 0.028 | | | Linear Fit | 0.019 |

The results of this test show that neither the pager motor nor the ZipZap motor could have supplied enough torque to hold the mobile robot on more than a minimal slope. The ZipZap motor can provide 0.057 [mNm] at 3 V and the pager motor can supply 0.084 [mNm] at 3 V. Both motors could only hold the robot stationary on a 15 degree slope. The motor that was finally chosen for the prototype was one made by Namiki, model SBLO4-0829 with gearhead PG04-337. The motor runs on a nominal 3 V and can provide 10.6 [mNm] stall torque at 80 rpm. This motor provides a design factor of 4 for the robot on a 75-degree slope (if frictional force is sufficient to prevent sliding).

The motors chosen for this prototype included a control board, which needed a +5 V supply. The rotational speed of the motor was controlled with a potentiometer that acted as a voltage divider. For example, if the input to the motor was 0 V, the motor would not rotate, if the input was 5 V, the motor would rotate at top operational speed (according to the product specs). The relationship between voltage and speed was not linear, as the motor did not start rotating until the voltage reaches more than 1.5 V.

The potentiometer on the control board had three terminals. The resistance between the two base terminals was a constant 1.021 k Ohms. The resistance between each base terminal and the third terminal was dependent on the position of the adjustment screw; if the screw was turned clockwise, one resistance increased, while the other decreased. If the screw was turned counterclockwise, the opposite was true. In both cases, the sum of the two resistances was always 1.021 k Ohms. It is this relationship between the terminals that created the voltage divider.

In addition to controlling speed of the motor, the control board allowed for the direction of rotation to be changed. One of the inputs to the board accepted a logic signal (0 or +5 V). If the signal was a logic “0,” the motor spun in one direction. If the signal was a logic “1,” the motor spun in the other direction.

It was clear to see that using a screwdriver to alter the speed of the motors was not a practical method of control. Thus, thumb sticks on a Playstation™ Dual-Shock controller were used to operate the motors. Each Playstation™ controller had two analog thumb sticks, each with two degrees of freedom. This essentially allowed the operator to move the thumbsticks a finite amount in an XY coordinate plane (though truly it was an X- and Y-rotation, it was so limited that the stick basically stayed in the XY plane). Each direction (X and Y) was controlled by a separate potentiometer; thus, pushing the stick forward a little yielded a different output than pushing the stick forward a great deal.

This method of control described herein is far superior to a directional pad (or D-pad). A D-pad type of control can be found on the original Nintendo™ game system. The pad looks like a plus sign (+), and has four discrete directions. For example, if one pushes up on the pad, the result is a logic “1” in that direction. Such a method of control works fine if one has no need for speed control. With an analog thumb stick, instead of all or nothing, movement can be sped up or slowed down according to how far the stick is pushed in the corresponding direction. This type of control is what was needed for the motors for this embodiment of this invention. However, as each motor had only one degree of rotational freedom, only one degree was needed for each of the thumb sticks. Thus, only the Y direction potentiometer was used.

To connect the Playstation™ controller, each potentiometer on the motor control boards was removed. A triangular resistor network was then created for each motor where the thumb sticks comprised one side and 1 k resistors comprised the other two sides. These networks were then soldered onto the control boards. When power was applied to the control board, the speed of each motor could be increased by pushing the respective thumb stick forward. Another feature of the Playstation™ controller was the “Z” button. Each controller had two buttons that were pushed by depressing the thumb sticks. Each thumb stick had three degrees of freedom: X- and Y-rotation, and translation in the Z-direction (albeit limited translation as it is a digital button). This button on the controller turned out to be quite useful as it was wired to control the direction of each motor. By connecting +5 v to one side of the button and the other side to the control board, it was possible to choose in which direction the motors rotated, i.e., push the thumb stick forward and the motor spun one way; push the thumb stick in, and then forward, and the motor spun the other way.

Next, a circuit was designed that allowed the user to push the thumb sticks forward to make the wheels spin forward, and backward to make the wheels spin backward, so that the thumb sticks no longer had to be depressed to change direction. The new design allowed a greater range of speed control and the ability to compensate for motor operational differences. The new design was much more complex than the control setup used in the initial prototypes, making control of the robot much easier.

Testing was conducted on the mobile robot. The weight of the robot, W, was 1.0 oz. The radius of the two wheels was 7.5 mm, and they were made of aluminum. Experiments were conducted on top of four types of objects: a tabletop, a mouse pad, particleboard and sliced beef liver. The robot was placed on top of each of these objects and the maximum friction force, F, was measured. The force was measured using an Ohaus Spring Scale with one-quarter ounce divisions. The force was approximated to the nearest 0.05 ounces. The coefficient of friction was determined by the formula $\mu$=F/W. Table 3 shows the four coefficients of friction measured by experiments.

TABLE 3

Friction Coefficients on Various Surfaces

| | Maximum Friction Force (oz.) | Coefficient of Friction |
|---|---|---|
| Table | 0.05 | 0.050 |
| Mouse pad | 0.65 | 0.65 |
| Particle board | 0.2 | 0.2 |
| Beef liver | 0.1 | 0.1 |

The robot was driven on a slope, which was increased from zero degrees until the robot could no longer move. The result showed that the practical maximum angle of slope was about 40 degrees. There was enough torque in the motors to power the robot at higher angles, but the friction between the wheels and the surface was not great enough to allow the robot to maintain traction once the slope got above 40 degrees.

Figure 7:
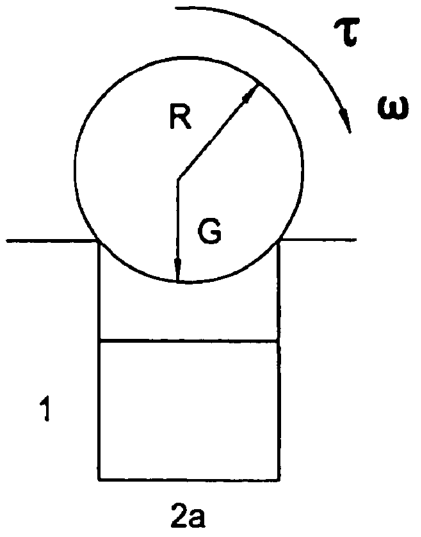
FIG. 7 is an elastic body model used in friction analysis of the mobile robot.

The performance of the robot was tested in the body of a pig, and problems were encountered due to the lack of traction of the robot on the organs, and due to the softness of the organs. Mainly the problems resulted from the lack of frictional force, that is, the friction was not high enough to provide resistance to the torque provided by the wheel motor. This problem was addressed through the force analysis based on an elastic foundation, i.e., where the mobile robot was assumed to roll on an elastic surface (see FIG. 7). In this model, friction resistance to rolling is largely due to the hysteresis from deformation of the foundation. In the contact portion, the elastic force δ(x) was assumed to be the normal distribution function of x. Here x range was from −a to a. The following equation was derived:

$$\frac{G}{2aL} = \int_{-a}^{a} \delta(x)dx$$

Then from the equation above, $$\delta(x) = \frac{2G}{\pi a}\left[1 - \left(\frac{x}{d}\right)^2\right]^{\frac{1}{2}}$$

Thus, the sum of partial differential friction force:

$$\Sigma f = \delta(\theta)\cos(\theta) + \tau(\theta)\sin(I)$$

By the integral calculation, one can get the friction force:

$$f = \frac{4}{3}\left(\frac{W}{\pi}\right)^{3/2} \frac{1}{\sqrt{R}} \sqrt{\frac{1 - v^2}{\Sigma}}$$

Where Σ is the Young's modulus and R is the Poisson's ratio.

In order to give the robot the capability to move well on a smooth, sloped or bumpy surface, the frictional force needed to be increased. From the force analysis, it was determined that the frictional force was proportional to the weight and inversely proportional to the radius of the wheel. Therefore, the following two methods are feasible and may be adopted. First, the mass of the robot could be increased. One good way to do so is to change the material of the wheels. In the initial design, aluminum was used which made the robot lighter than if steel had been used. Second, the radius of the wheels might be reduced. A smaller radius of the wheels also would increase the frictional force. The radius of the wheels could be reduced in a couple of ways. First, the wheels might be designed to have a smaller diameter; however, this solution is not the optimal solution as the space for the motor and electrical components is minimal and a smaller wheel diameter would reduce this space even further. Another solution is to add treads to the wheels. Alternatively, the tips of the treads may have a smaller radius without reducing the diameter of the wheel itself.

EXAMPLE 2

Manipulator Arm Design

The design process of the manipulator arm resulted in a working prototype. The original design was illustrated using a three-dimensional (3D) computer-aided-drafting (CAD) file using Solid Works® 2001. Utilizing the CAD program, the linkages, motors and camera were drawn with accurate dimensions.

Figure 8:
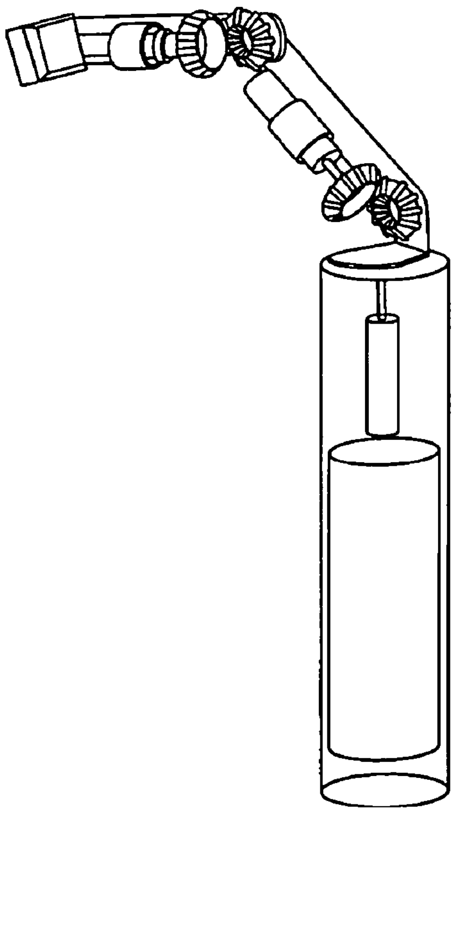
FIG. 8 is a CAD drawing of one embodiment of a manipulator arm according to the present invention.

The initial designs for one embodiment of the invention included the idea of conserving space by attaching motors to the linkages. Using miter gears, the rotational force of the motors was transmitted 90 degrees to rotate each link. The CAD drawing shown in FIG. 8 illustrates the initial design with all pieces drawn to scale. The CAD design was a big step in determining the lengths of each linkage and how the size of each component would relate to one another. The miter gears are a stock product from Stock Drive Products/Sterling Instruments. The initial CAD design allowed determination of the dimensions for the motor and camera; thus, each of the two linkages could be designed to fit around each motor in order to provide adequate space for the wires and other attachments. The dimensions of the linkages permitted weight calculation for each linkage as well as the torque required by each motor to rotate the two linkages.

Figure 9:
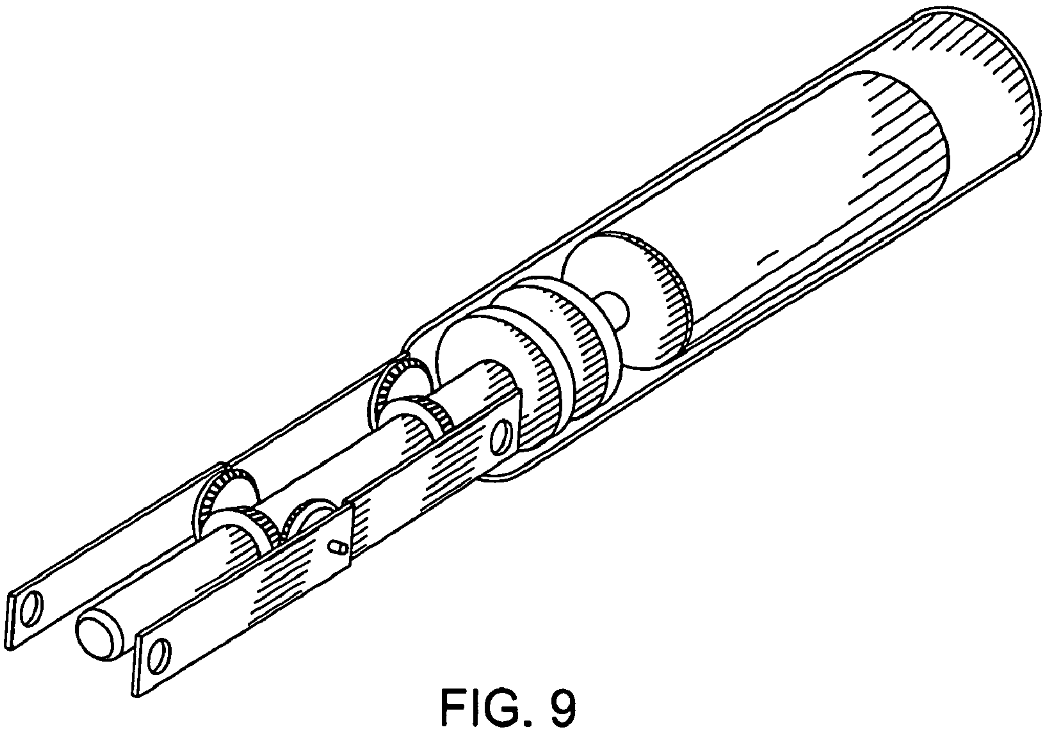
FIG. 9 is a CAD drawing of another embodiment of a manipulator arm according to the present invention.

After performing numerous calculations, the linkages were designed to be stronger. With the addition of another set of linkages as shown in FIG. 9, linkage strength was increased compared to the previous design. On the other hand, the lifting capacity was diminished due to the additional weight of the extra set of links. However, an important advantage of the design (again, see FIG. 9) was the smaller bending moment created during the applied torque. This was believed to be a major problem with the manipulator arm shown in FIG. 8, as the point in which the entire linkage attaches and rotates is supported only by the shaft of the bottom motor. The additional set of linkages created two points of rotation about which the linkages are rotated. The farther apart the two attachments were, the stronger the structure was determined to be.

The ramifications of the added weight from the second set of linkages were considered, as was the construction process and material fabrication. From a materials point of view, aluminum was initially chosen as a light, strong, and relatively easy material to machine. The cost of aluminum was not a consideration since the pieces were so small.

Figure 10:
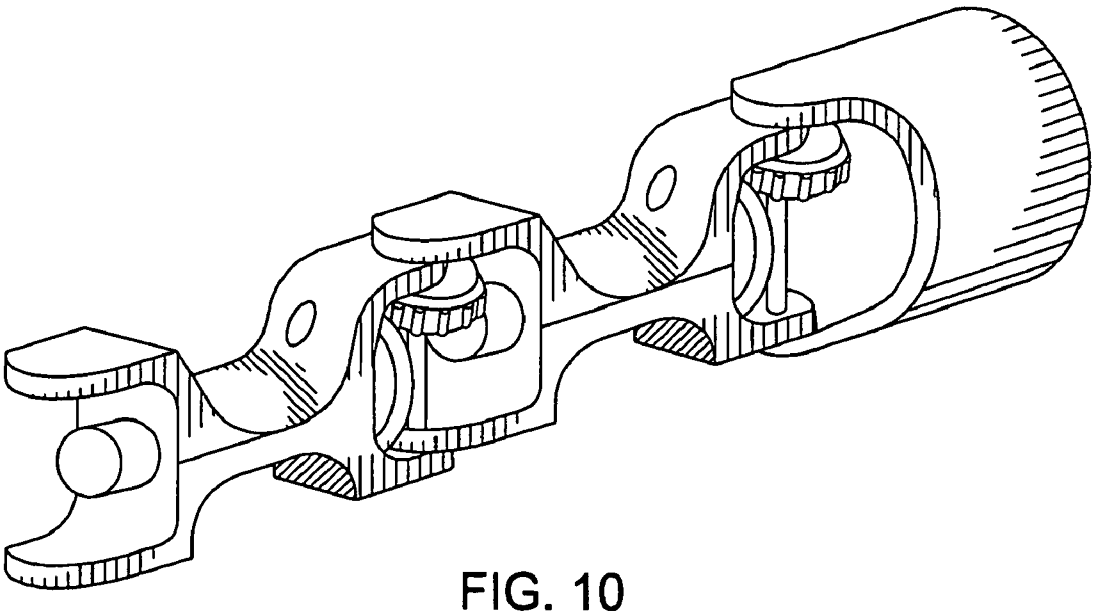
FIG. 10 is a CAD drawing of yet another embodiment of a manipulator arm according to the present invention

At this stage in the design, the problem of attaching the motors to the linkages became a major concern. Several methods for securing the motors in place involved pinning, taping, bolting, clamping, or gluing. One solution that seemed to make sense, as well as save time in machining and complicated attachment configurations, was to use stereolithography to make the linkages. Stereolithography not only allows for the design of many complicated configurations, but also provides great precision. FIG. 10 represents the third design idea, which utilized stereolithography to construct the linkages and the base section out of a cured resin material similar to plastic.

With the use of stereolithography, almost any kind of linkage configurations could be designed. Linkage assembly was prioritized at this point. This embodiment shows the linkages on the top slightly different from those on the bottom so that when they are matched up, they form a whole linkage. This allows the motors and gears to be placed in one linkage while the other linkage can then be attached at a later time.

Figure 11:
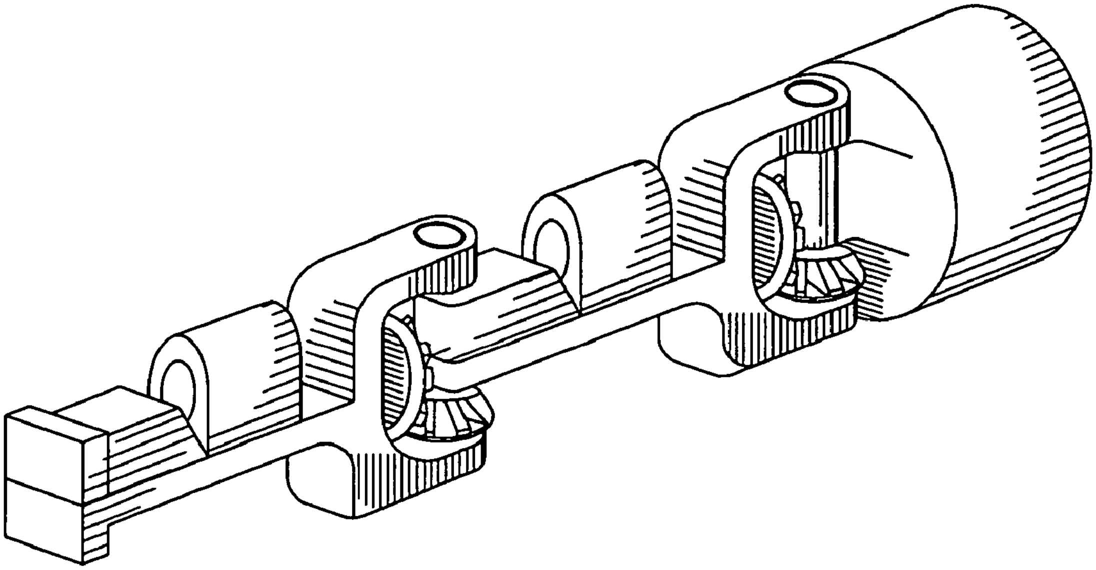
FIG. 11 is a CAD drawing of yet another embodiment of a manipulator arm according to the present invention.

The next step in the design process involved making the linkages strong and durable. This was an important consideration since stereolithography material is not as tough as aluminum. The point at which the linkage connects to the shaft is the weakest area of the linkage. However, it is difficult to strengthen the linkages while leaving enough space for the motors and miter gears. A solution to this problem took on a completely different approach to connecting one linkage to another when compared to previous designs. FIG. 11 illustrates another design, where the base attachment is placed inside the linkage. Essentially, the linkages are like male and female components that fit together in only one way and use less space.

Figure 12:
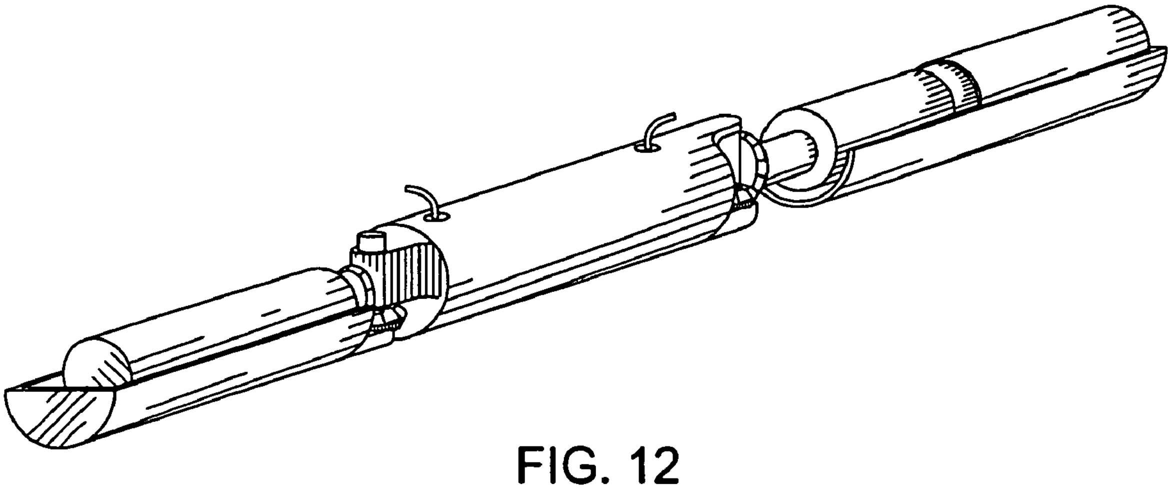
FIG. 12 is a CAD drawing of yet another embodiment of the manipulator arm according to the present invention.

The next hurdle in the linkage design came about when it was determined that the motors could be extremely difficult, if not impossible, to control precisely. An additional problem was the weight of the linkages. In order to make the linkages stronger, they were designed to be thicker, which resulted in heavier loads for the motors to move. The solution to the motor control problem was solved by using larger motors with encoders from Faulhaber Company. The new motors allowed control of the motion of each link, as well as provided much more torque than the original, smaller motors. However, the linkages had to be redesigned in order to accommodate the larger motor size. FIG. 12 illustrates the final design of the manipulator arm.

Figure 13:
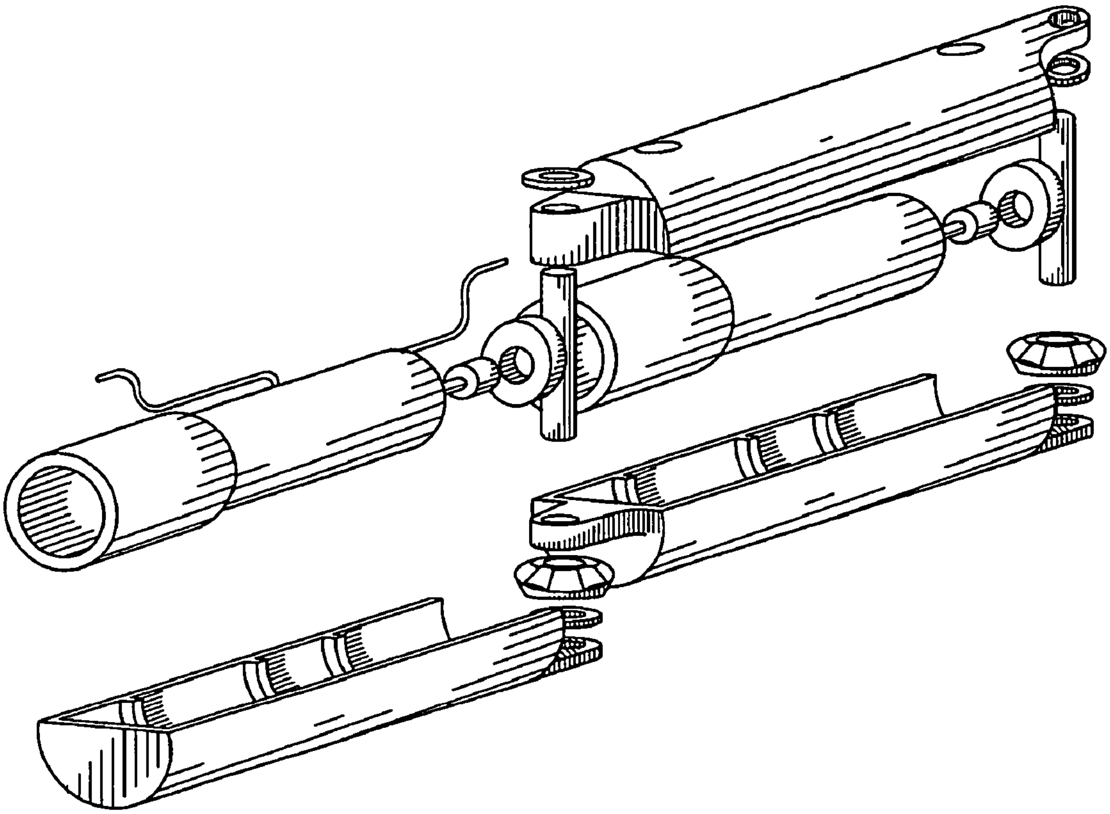
FIG. 13 is an expanded CAD drawing of the embodiment of a manipulator arm shown in FIG. 12.

The final design of the linkages, shown in FIG. 12, illustrates the drastically increased size in comparison to FIG. 11. However, the concept essentially is the same, i.e., the linkages are composed of two halves that attach in only one configuration. FIG. 13 shows a more detailed look at the two linkages and all of the components.

The design of the linkages utilizing stereolithography allowed a great deal of latitude in addressing several problems at once. However, drawbacks to stereolithography include cost, time of construction, and tolerances of the cured pieces. Overall, the manipulator robot design was a success and provides an important element for the use of robots in minimally invasive surgical manipulations.

Figure 14:
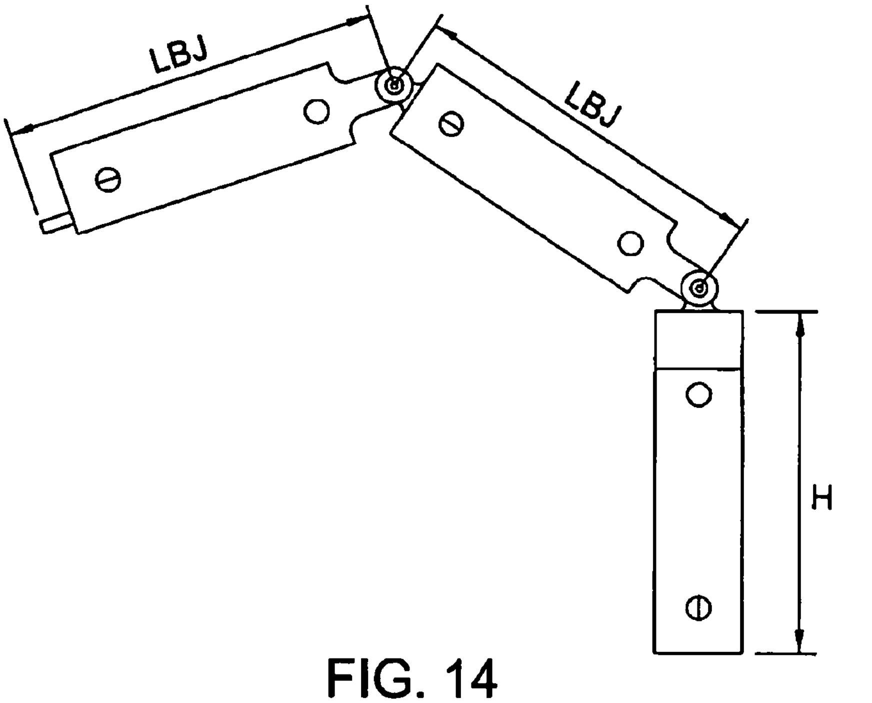
FIG. 14 is a model of the manipulator arm used to determine the Jacobian.

When performing a velocity analysis of a mechanism, in this case the manipulator arm, it was helpful to define a matrix quantity called the Jacobian. The Jacobian specifies a mapping from velocities in joint space to velocities in Cartesian space. The Jacobian can be found for any frame and it can be used to find the joint torques, discussed infra. FIG. 14 shows the manipulator drawing used to find the Jacobian. For additional information on the Jacobian, see "Introduction to Robotics" by John J. Craig.

The fundamental equations used in finding the Jacobian are:

$$^{i+1}V_{i+1} = {}^{i+1}_{i}R \cdot ({}^{i}V_i + {}^{i}\omega_i \times {}^{i}P_{i+1})$$

$$^{i+1}\omega_{i+1} = {}^{i+1}_{i}R \cdot {}^{i}\omega_i + \theta^{\&}_{i+1} \cdot {}^{i+1}Z_{i+1}$$

$$^{i}V = {}^{i}J(\theta)\theta^{\&}$$

$$^{0}_{1}R = \begin{bmatrix} c\theta_1 & -s\theta_2 & 0 \\ s\theta_1 & c\theta_1 & 0 \\ 0 & 0 & 1 \end{bmatrix} \Rightarrow {}^{1}_{0}R = \begin{bmatrix} c\theta_1 & s\theta_1 & 0 \\ -s\theta_1 & c\theta_1 & 0 \\ 0 & 0 & 1 \end{bmatrix}$$

$$^{1}_{2}R = \begin{bmatrix} 0 & -1 & 0 \\ 0 & 0 & -1 \\ 1 & 0 & 0 \end{bmatrix}.$$

$$\begin{bmatrix} c\theta_2 & -s\theta_2 & 0 \\ s\theta_2 & c\theta_2 & 0 \\ 0 & 0 & 1 \end{bmatrix} = \begin{bmatrix} -s\theta_2 & -c\theta_2 & 0 \\ 0 & 0 & -1 \\ c\theta_2 & -s\theta_2 & 0 \end{bmatrix} \Rightarrow {}^{2}_{1}R = \begin{bmatrix} -s\theta_2 & 0 & c\theta_2 \\ -c\theta_2 & 0 & -s\theta_2 \\ 0 & -1 & 0 \end{bmatrix}$$

$$^{2}_{3}R = \begin{bmatrix} c\theta_3 & -s\theta_3 & 0 \\ s\theta_3 & c\theta_3 & 0 \\ 0 & 0 & 1 \end{bmatrix} \Rightarrow {}^{3}_{2}R = \begin{bmatrix} c\theta_3 & s\theta_3 & 0 \\ -s\theta_3 & c\theta_3 & 0 \\ 0 & 0 & 1 \end{bmatrix}$$

For link 1, $$i = 0\,{}^{1}V_1 = {}^{1}_{0}R \cdot ({}^{0}V_0 + {}^{0}\omega_0 \times {}^{0}P_1) = 0$$

$$^{1}\omega_1 = {}^{1}_{0}R \cdot {}^{0}\omega_0 + \theta^{\&}_1 \cdot {}^{1}z_1 = \begin{bmatrix} 0 \\ 0 \\ \theta^{\&}_1 \end{bmatrix}$$

For link 2, $$i = 1\,{}^{2}V_2 = {}^{2}_{1}R \cdot ({}^{1}V_1 + {}^{1}\omega_1 \times {}^{1}P_2) = 0$$

-continued $$^{2}\omega_2 = {}^{2}_{1}R \cdot {}^{1}\omega_1 + \theta^{\&}_2 \cdot {}^{2}z_2 = \begin{bmatrix} \theta^{\&}_1 \cdot c\theta_2 \\ -\theta^{\&}_1 \cdot s\theta_2 \\ \theta^{\&}_2 \end{bmatrix}$$

For link 3, $i = 2$ $$^{3}V_2 = {}^{3}_{2}R \cdot ({}^{2}V_2 + {}^{2}\omega_2 \times {}^{2}P_3) = \begin{bmatrix} L_1 \cdot \theta^{\&}_2 \cdot s\theta_3 \\ L_1 \cdot \theta^{\&}_2 \cdot c\theta_3 \\ L_1 \cdot \theta^{\&}_1 \cdot s\theta_2 \end{bmatrix}$$

$$^{3}\omega_3 = {}^{3}_{2}R \cdot {}^{2}\omega_2 + \theta^{\&}_3 \cdot {}^{3}z_3 = \begin{bmatrix} \theta^{\&}_1 \cdot c\theta_2 \cdot c\theta_3 - \theta^{\&}_1 \cdot s\theta_2 \cdot s\theta_3 \\ -\theta^{\&}_1 \cdot c\theta_2 \cdot s\theta_3 - \theta^{\&}_1 \cdot s\theta_2 \cdot c\theta_3 \\ \theta^{\&}_2 + \theta^{\&}_3 \end{bmatrix}$$

For link 4, $i = 3$ $$^{4}V_4 = {}^{4}_{3}R \cdot ({}^{3}V_3 + {}^{3}\omega_3 \times {}^{3}P_4) = L \begin{bmatrix} \theta^{\&}_2 \cdot s\theta_3 \\ \theta^{\&}_2 \cdot (c\theta_3 + 1) \cdot s\theta_3 + \theta^{\&}_3 \\ \theta^{\&}(c\theta_2 s\theta_3 + s\theta_2 c\theta_3 + s\theta_2) \end{bmatrix}$$

$$^{0}V_4 = {}^{0}_{4}R \cdot {}^{4}V_4 = {}^{0}_{1}R \cdot {}^{1}_{2}R \cdot {}^{2}_{3}R \cdot {}^{3}_{4}R \cdot {}^{4}V_4$$

$$^{0}_{4}R = \begin{bmatrix} -c\theta_1 \cdot c\theta_2 \cdot s\theta_3 - c\theta_1 \cdot s\theta_2 \cdot c\theta_3 & -c\theta_1 \cdot c\theta_2 \cdot c\theta_3 + c\theta_1 \cdot s\theta_2 \cdot s\theta_3 & s\theta \\ -s\theta_1 \cdot c_2 \cdot s\theta_3 - s\theta_1 \cdot s\theta_2 \cdot c\theta_3 & -s\theta_1 \cdot c\theta_2 \cdot c\theta_3 + s\theta_1 \cdot s\theta_2 \cdot s\theta_3 & -c\theta_1 \\ 0 & -c\theta_2 \cdot s\theta_3 - s\theta_2 \cdot c\theta_3 & 0 \end{bmatrix}$$

$$^{0}V_4 = L \cdot \begin{bmatrix} s_1 \cdot \begin{pmatrix} c_2 \cdot s_3 + \\ s_2 \cdot c_3 + s_2 \end{pmatrix} & c_1 \cdot \begin{pmatrix} s_2 \cdot s_3 - \\ c_2 \cdot c_3 - c_2 \end{pmatrix} & c_1 \cdot (s_2 \cdot s_3 - c_2 \cdot c_3) \\ -c_1 \cdot \begin{pmatrix} c_2 \cdot s_3 + \\ s_2 \cdot c_3 + s_2 \end{pmatrix} & s_1 \cdot \begin{pmatrix} s_2 \cdot s_3 - \\ c_2 \cdot c_3 - c_2 \end{pmatrix} & s_1 \cdot (s_2 \cdot s_3 - c_2 \cdot c_3) \\ 0 & -s_2 \cdot c_3 - c_2 \cdot s_3 - s_2 & -c_2 \cdot s_3 - s_2 \cdot c_3 \end{bmatrix} \cdot \begin{bmatrix} \theta^{\&}_1 \\ \theta^{\&}_2 \\ \theta^{\&}_3 \end{bmatrix}$$

$$^{0}J(\theta) = L \cdot \begin{bmatrix} (s_2 + s_{23})s_1 & -(c_2 + c_{23})c_1 & -c_{23}c_1 \\ -(s_2 + s_{23})c_1 & -(c_2 + c_{23})s_1 & -c_{23}s_1 \\ 0 & -s_2 - s_{23} & -s_{23} \end{bmatrix}$$

where $S_n$ sin $\theta_n c_n$=cos $\theta_n$, $s_{nm}$=sin($\theta_n$+$\theta_m$), $c_{nm}$=cos($\theta_n\theta_m$).

Figure 15:
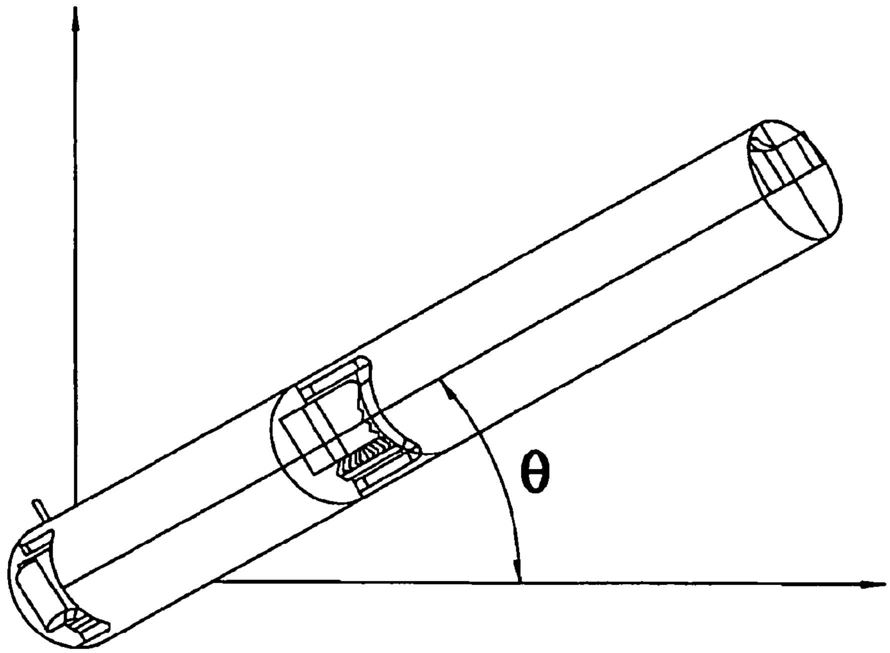
FIG. 15 is a top view of one embodiment of a manipulator arm according to the present invention.

The second method provides the results seen in FIG. 15. The x, y and z equations are for the tip of link 3.

$$z = L_1 + L_2 \cdot \cos\theta_2 + L_3 \cdot \cos(\theta_2 + \theta_3)$$

$$x = -[L_2 \cdot \sin\theta_2 + L_3 \cdot \sin(\theta_2 + \theta_3)] \cdot \cos\theta_1$$

$$y = -[L_2 \cdot \sin\theta_2 + L_3 \cdot \sin(\theta_2 + \theta_3)] \cdot \sin\theta_1$$

$$^{0}J(\theta) = \begin{bmatrix} \frac{\partial x}{\partial \theta_1} & \frac{\partial x}{\partial \theta_2} & \frac{\partial x}{\partial \theta_3} \\ \frac{\partial y}{\partial \theta_1} & \frac{\partial y}{\partial \theta_2} & \frac{\partial y}{\partial \theta_3} \\ \frac{\partial z}{\partial \theta_1} & \frac{\partial z}{\partial \theta_2} & \frac{\partial z}{\partial \theta_3} \end{bmatrix}$$

-continued $$ {}^{0}J(\theta) = \begin{bmatrix} (L_2 s_2 + L_3 s_{23}) s_1 & -(L_2 c_2 + L_3 s_{23}) c_1 & -L_3 c_{23} c_1 \\ -(L_2 s_2 + L_3 s_{23}) c_1 & -(L_2 c_2 + L_3 s_{23}) s_1 & -L_3 c_{23} s_1 \\ 0 & -L_2 s_2 + L_3 s_{23} & -L_3 s_{23} \end{bmatrix} $$

where $s_n = \sin\theta_n$, $c_n = \cos_n$, $S_{nm} = \sin(\theta_n + \theta_m)$, $C_{nm} = \cos(\theta_n + \theta_m)$ since $L_1 = L_2 = L$ $$ {}^{0}J(\theta) = L \cdot \begin{bmatrix} (s_2 + s_{23}) s_1 & -(c_2 + c_{23}) c_1 & -c_{23} c_1 \\ -(s_2 + s_{23}) c_1 & -(c_2 + c_{23}) s_1 & -c_{23} s_1 \\ 0 & -s_2 - s_{23} & -s_{123} \end{bmatrix} $$

The motor selected for the manipulator was a DC Micromotor manufactured by Faulhaber Company. It is the smallest motor available that could provide adequate torque with the use of planetary gears. There are several types of motors available depending on nominal voltage. The manipulator can use a low voltage motor, such as a 3 V motor. However, due to time constraints and in-stock availability, a 6 V motor was chosen and tested. The 6 V motor had a 15,800 rpm no-load speed, 0.057 oz-in stall torque, and weighed 0.12 oz. The motor had an 8 mm diameter and it was 16 mm long. Due to its high no-load speed, a precision gearhead was required.

The only precision gearhead available for the motor selected was a planetary gearhead. There are several reduction ratios (ranging from 4:1 to 4,096:1) available depending on the application. Gearhead dimensions vary depending on the reduction ratio. For the preliminary analysis, a gearhead with a reduction ratio of 256:1 was selected. It has an 8 mm diameter, is 17.7 mm long, and weighs 0.19 oz.

An encoder was needed for the indication and control of both shaft velocity and the direction of rotation, as well as for positioning. A 10 mm magnetic encoder was chosen for this particular application. It was 16.5 mm long, but it only added 11.5 mm to the total length of the assembly. The weight of the encoder was assumed to be 0.1 oz. The encoder provided two channels (A and B) with a 90° phase shift, which are provided by solid-state Hall sensors and a low inertia magnetic disc. Table 1 shows a summary of motor, planetary gearhead, and encoder properties.

TABLE 4

Summary of motor properties

| | Mass (m) | Length (L) |
|---|---|---|
| Motor (M) Series 0816 006 S | 0.12 oz | 16 mm |
| Planetary Gearhead (G) Series 08/1 Ratio 256:1 | 0.19 oz | 17.7 mm |
| Encoder (E) Type HEM 0816 | ≈0.1 oz | 11.5 mm |
| Total | 0.41 oz | 45.2 mm |

$L_T = L_M + L_{PG} + L_E = 45.2$ $m_T = m_M + m_{PG} + M_E = 0.41$ oz $$ m_T = 0.41 \text{ oz} \times 28.3495 \frac{\text{g}}{\text{oz}} = 11.623 \text{ g} $$

Figure 16:
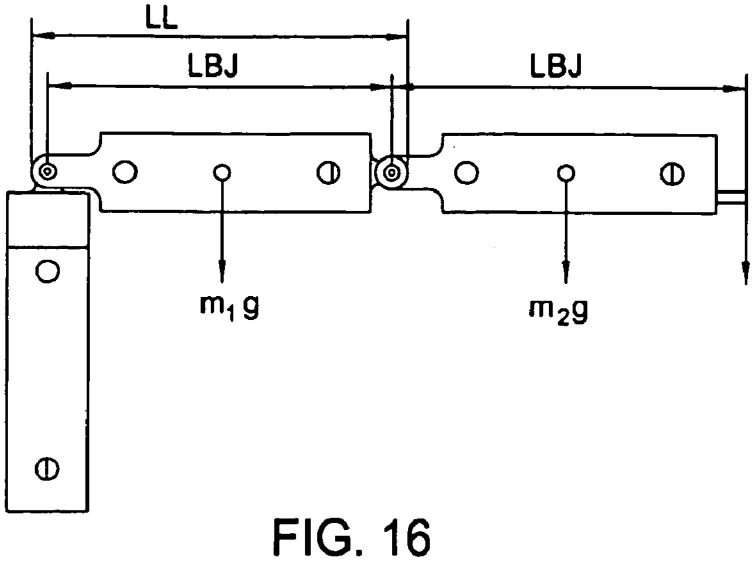
FIG. 16 is a model of one embodiment of a manipulator arm according to the present invention labeled with the parameters used to determine properties of the links.

FIG. 16 shows a drawing of the manipulator with $L_L$, $L_{BJ}$, $M_1$, $M_2$, $m_1 g$, $m_2 g$ and $W_p$ labeled.

TABLE 5

Summary of Link Properties

| Link Properties | |
|---|---|
| Length, $L_L$ (=$L_2$ = $L_3$) | 60 mm |
| Length between joints, $L_{BJ}$ | 59.5 mm |
| Outside diameter, $D_o$ | 12 mm |
| Inside diameter, $d_i$ | 8 mm |
| Wall thickness, t | 2 mm |
| Density, ρ | 1.18 g/cm$^3$ |

Figure 17:
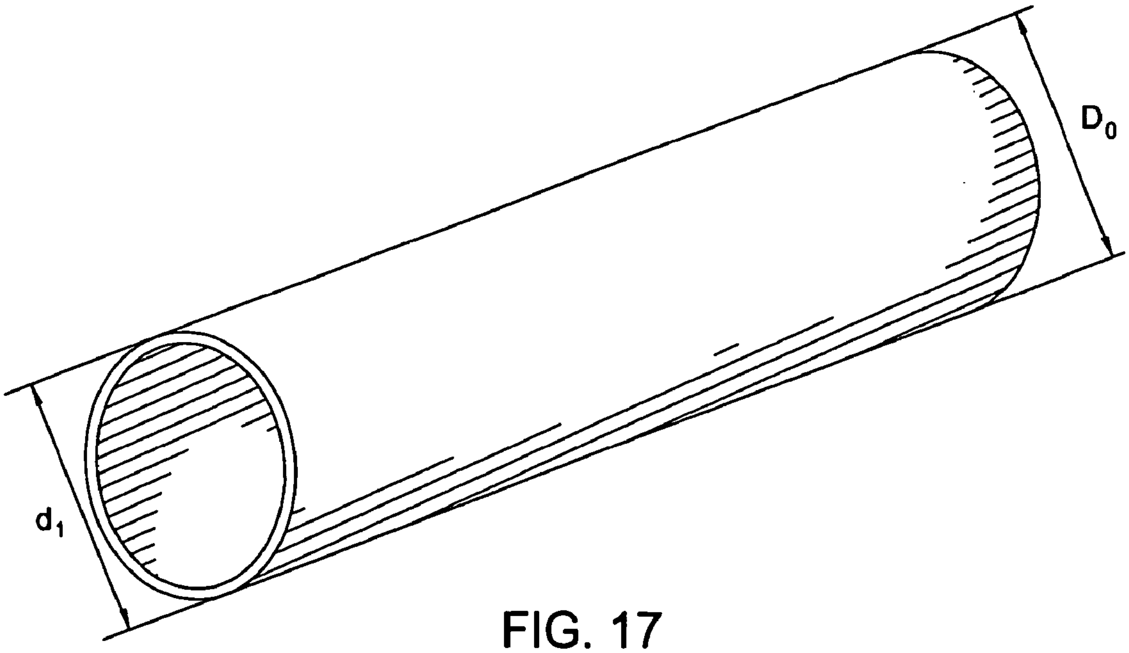
FIG. 17 is a representation of the link shape assumed to calculate moment.

It was assumed that the links were cylindrical tubes, as shown in FIG. 17.

Link Volume:

$$ V_L = \frac{D_o^2}{4} \cdot L_L - \frac{d_i^2}{4} \cdot (L_1 - 2t) $$

$$ \begin{aligned} V_L &= \frac{(12 \text{ mm})^2}{4} \times 60 \text{ mm} - \frac{(8 \text{ mm})^2}{4} \times (60 - 2 \times 2) \text{ mm} \\ &= 2160 \text{ mm}^3 - 896 \text{ mm}^3 \\ &= 1264 \text{ mm}^3 \end{aligned} $$

Link Mass:

$$ m_L = \rho \cdot V_L $$

$$ \begin{aligned} m_L &= 1.18 \frac{8}{\text{cm}^3} \times \frac{\text{cm}^3}{(10 \text{ mm})^3} \times 1264 \text{ mm}^3 \\ &= 1.49152 \text{ g} \end{aligned} $$

Total Weight of Motor and Link:

$$ m = m_T + m_L $$

$$ \begin{aligned} m &= 11.6233 \text{ g} + 1.49152 \text{ g} \\ &= 13.1148 \text{ g} \end{aligned} $$

$$ \begin{aligned} m_1 &= m_2 \\ &= m \end{aligned} $$

Payload Mass:

mρ=5 g

Moment Calculations (Refer to FIG. 16):

$$ M_1 = m_1 \cdot g \cdot \frac{L_1}{2} + m_2 \cdot g \cdot \left(L_1 + \frac{L_2}{2}\right) + m_3 \cdot g \cdot (L_1 + L_2) $$

$$ \begin{aligned} \text{Since } L_1 &= L_2 \\ &= L \end{aligned} $$

$$ M_1 = \left(\frac{m_1}{2} + \frac{3 \cdot m_2}{2} + 2 \cdot m_3\right) \cdot g \cdot L_{BJ} $$

$$ M_1 = \left(\frac{13.1148}{2} g + \frac{3 \cdot 13.1148}{2} g + 2 \cdot 5g\right) \cdot 9.81 $$

-continued $$\frac{m}{s^2}\cdot 59.5\ \text{mm}\cdot\frac{1m}{1000\ \text{mm}}\cdot\frac{1\ \text{kg}}{1000\ \text{g}}$$

$$M_1 = 0.21147\ \text{kg}\cdot\frac{m}{s^2}\cdot m$$

$$= 0.021147 N\cdot m$$

$$= \underline{\underline{21.147 mN\cdot m}}$$

$$M_2 = m_2\cdot g\cdot\frac{L_2}{2} + m_3\cdot g\cdot L_2$$

$$M_2 = \left(\frac{M_2}{2} + m_3\right)\cdot g\cdot L_{BJ}$$

$$M_2 = \left(\frac{13.1148}{2}g + 5\ \text{g}\right)\cdot 9.81\frac{m}{s^2}\cdot 59.5\ \text{mm}\cdot\frac{1m}{1000\ \text{mm}}\cdot\frac{1\ \text{kg}}{1000\ \text{g}}$$

-continued $$M_2 = 0.006746\ \text{kg}\cdot\frac{m}{s^2}\cdot m$$

$$= 0.006746 N\cdot m$$

$$= \underline{\underline{6.746 mN\cdot m}}$$

The maximum torque allowed by the motor for a continuous operation is 8.5 oz-in, which is 0.41 mNm. Using the reduction ratio of 256:1, the maximum torque allowed is 104.86 mNm (256×0.41 mNm). Clearly, this precision gearhead will provide plenty of torque. In order to optimize the manipulator design, precision gears with other reduction ratios may be used. Tables with calculations for lower reduction ratios are provided below. After comparing all the precision gearheads, it was determined that the reduction ratio of 64:1 provides sufficient torque while optimizing the design.

TABLE 6

Gear Reduction Ratios

| | Weight (oz) | Weight (g) | Length (mm) |
|---|---|---|---|
| **Link 1** | | | |
| Motor | 0.12 | 3.40194 | 16 |
| Planetary gears | 0.16 | 4.53592 | 15 |
| Encoder | 0.1 | 2.83495 | 11.5 |
| Total | 0.38 | 10.77281 | 42.5 |
| Link length (mm) = Length + 15 = | 57.5 | | |
| Length between joints (mm) = Link length − 0.5 = | 57 | | |
| Outside diameter, $D_o$ (mm) = | 12 | | |
| Inside diameter, $d_i$ (mm) = | 8 | | |
| Wall thickness, t (mm) = | 2 | | |
| Density of resin, ro ($g/cm^3$) = | 1.18 | | |
| Volume of link, V ($mm^3$) = | 1214 | | |
| Weight of link, m (g) = | 1.43252 | | |
| Weight of motor and link, m_tot (g) = | 12.20533 | | |
| **Link 2** | | | |
| Motor | 0.12 | 3.40194 | 16 |
| Planetary gears | 0.16 | 4.53592 | 15 |
| Encoder | 0.1 | 2.83495 | 11.5 |
| Total | 0.38 | 10.77281 | 42.5 |
| Link length (mm) = Length + 15 = | 57.5 | | |
| Length between joints (mm) = Link length − 0.5 = | 57 | | |
| Outside diameter, $D_o$ (mm) = | 12 | | |
| Inside diameter, $d_i$ (mm) = | 8 | | |
| Wall thickness, t (mm) = | 2 | | |
| Density of resin, ro ($g/cm^3$) = | 1.18 | | |
| Volume of link, V ($mm^3$) = | 1214 | | |
| Weight of link, m (g) = | 1.43252 | | |
| Weight of motor and link, m_tot (g) = | 12.20533 | | |
| Weight of camera or tool, m_c (g) = | 5 | | |
| Moment around joint 2, M1 (mNm) = | 19.24140875 | | |
| Moment around joint 3, M2 (mNm) = | 6.2082771 | | |
| Link length, L1 (mm) = | 57.5 | | |
| Link length, L2 (mm) = | 57.5 | | |
| Maximum moment, M_max (mNm) = | 19.24 | | |
| Maximum torque allowed, M_max_all (oz-in) = | 8.5 | =60.027 | MNm |
| is M_max > M_max_all? | NO | | |
| Maximum torque possible, M_max_pos (mNm) = | Gear Ratio | * Motor Torque = | 26.214144 |
| Is M_max_pos > M_max? | | YES | |
| This motor can be used to move the links. | | | |

TABLE 7

| Gear Reduction Ratios | Weight (oz) | Weight (g) | Length (mm) |
|---|---|---|---|
| Link 1 | | | |
| Motor | 0.12 | 3.40194 | 16 |
| Planetary gears | 0.19 | 5.386405 | 17.7 |
| Encoder | 0.1 | 2.83495 | 11.5 |
| Total | 0.41 | 11.623295 | 45.2 |
| Link length (mm) = Length + 15 = | 60.2 | | |
| Length between joints (mm) = Link length − 0.5 = | 59.7 | | |
| Outside diameter, $D_o$ (mm) = | 12 | | |
| Inside diameter, $d_i$ (mm) = | 8 | | |
| Wall thickness, t (mm) = | 2 | | |
| Density of resin, ro (g/cm$^3$) = | 1.18 | | |
| Volume of link, V (mm$^3$) = | 1268 | | |
| Weight of link, m (g) = | 1.49624 | | |
| Weight of motor and link, m_tot (g) = | 13.119535 | | |
| Link 2 | | | |
| Motor | 0.12 | 3.40194 | 16 |
| Planetary gears | 0.19 | 5.386405 | 17.7 |
| Encoder | 0.1 | 2.83495 | 11.5 |
| Total | 0.41 | 11.623295 | 45.2 |
| Link length (mm) = Length + 15 = | 60.2 | | |
| Length between joints (mm) = Link length − 0.5 = | 59.7 | | |
| Outside diameter, $D_o$ (mm) = | 12 | | |
| Inside diameter, $d_i$ (mm) = | 8 | | |
| Wall thickness, t (mm) = | 2 | | |
| Density of resin, ro (g/cm$^3$) = | 1.18 | | |
| Volume of link, V (mm$^3$) = | 1268 | | |
| Weight of link, m (g) = | 1.49624 | | |
| Weight of motor and link, m_tot (g) = | 13.119535 | | |
| Weight of camera or tool, m_c (g) = | 5 | | |
| Moment around joint 2, M1 (mNm) = | 21.2236650 | | |
| Moment around joint 3, M2 (mNm) = | 6.77005875 | | |
| Link length, L1 (mm) = | 60.2 | | |
| Link length, L2 (mm) = | 60.2 | | |
| Maximum moment, M_max (mNm) = | 21.22 | | |
| Maximum torque allowed, M_max_all (oz-in) = | 8.5 | =60.027 | MNm |
| is M_max > M_max_all? | NO | | |
| Maximum torque possible, M_max_pos (mNm) = | Gear Ratio | * Motor Torque = | 104.85658 |
| Is M_max_pos > M_max? | | YES | |
| This motor can be used to move the links. | | | |

By using the Jacobian that was previously developed and is shown below, it is possible to calculate the torques provided by the force exerted to the tip of the manipulator. However, this method does not take into account the weights of links and motors.

$$ {}^0J(\theta) = L\cdot\begin{bmatrix} (s_2+s_{23})s_1 & -(c_2+c_{23})c_1 & -c_{23}c_1 \\ -(s_2+s_{23})c_1 & -(c_2+c_{23})s_1 & -c_{23}s_1 \\ 0 & -s_2-s_{23} & -s_{23} \end{bmatrix} $$

$$ f = \begin{bmatrix} 0 \\ 0 \\ -f_z \end{bmatrix} \text{ where } f_z = $$

$$ 0.005\text{ kg}\times 9.81\frac{m}{s^2} = 0.04905N \text{ and } L = 59.5\text{ mm} $$

$$ {}^0\tau_j = {}^0J(\theta)^T\cdot f $$

$$ {}^0\tau_j = L\cdot\begin{bmatrix} (s_2+s_{23})s_1 & -(c_2+c_{23})c_1 & -c_{23}c_1 \\ -(s_2+s_{23})c_1 & -(c_2+c_{23})s_1 & -c_{23}s_1 \\ 0 & -s_2-s_{23} & -s_{23} \end{bmatrix}\cdot\begin{bmatrix} 0 \\ 0 \\ -f_z \end{bmatrix} $$

-continued $$ {}^0\tau_j = 59.5\text{ mm}\cdot\begin{bmatrix} (s_2+s_{23})s_1 & -(c_2+c_{23})c_1 & -c_{23}c_1 \\ -(s_2+s_{23})c_1 & -(c_2+c_{23})s_1 & -c_{23}s_1 \\ 0 & -s_2-s_{23} & -s_{23} \end{bmatrix}\cdot\begin{bmatrix} 0 \\ 0 \\ -0.4905N \end{bmatrix} = \begin{bmatrix} 0 \\ 2.918\cdot(s_2+s_{23}) \\ 2.918\cdot s_{23} \end{bmatrix} $$

Using $\theta_1 = 0^\circ$, $\theta_2 = 90^\circ$, $\theta_3 = 0^\circ$ $$ {}^0\tau_j = \begin{bmatrix} 0 \\ 5.836 \\ 2.918 \end{bmatrix} mN\cdot\text{m} $$

Thus the torque for the base motor is 0 mNm: for link 1 it is 5.836 mNm, and for link 2 it is 2.918 mNm. This result makes sense because the largest torque will be exerted on the joint farthest away from the tip of the manipulator. Also, since the distance is two times the distance to middle joint, the result is two times bigger.

Accounting for the link and motor masses, $$^{0}\tau_{LM}\begin{bmatrix} 0 \\ W_{LM}\cdot\left(\frac{L_1}{2}+\frac{3\cdot L_2}{2}\right) \\ W_{LM}\cdot\frac{L_2}{2} \end{bmatrix} = \text{m}\cdot\text{g}\cdot\text{L}\cdot\begin{bmatrix} 0 \\ 2 \\ \frac{1}{2} \end{bmatrix}$$

$$^{0}\tau_{LM} = 13.1148\ g\times 9.81\frac{\text{m}}{s^2}\times 59.5$$

$$\text{mm}\times\begin{bmatrix} 0 \\ 2 \\ \frac{1}{2} \end{bmatrix}\times\frac{1\text{m}}{1000\text{mm}}\times\frac{1\text{kg}}{1000\ \text{g}} = \begin{bmatrix} 0 \\ 15.31 \\ 3.828 \end{bmatrix} mN\cdot\text{m}$$

The total torque is, $$^{0}\tau = {}^{0}\tau_j + {}^{0}\tau_{LM} = \begin{bmatrix} 0 \\ 5.836 \\ 2.918 \end{bmatrix} + \begin{bmatrix} 0 \\ 15.31 \\ 3.828 \end{bmatrix} = \begin{bmatrix} 0 \\ 21.146 \\ 6.746 \end{bmatrix} mN\cdot\text{m}$$

As shown, both methods provide the same result.

Figure 18:
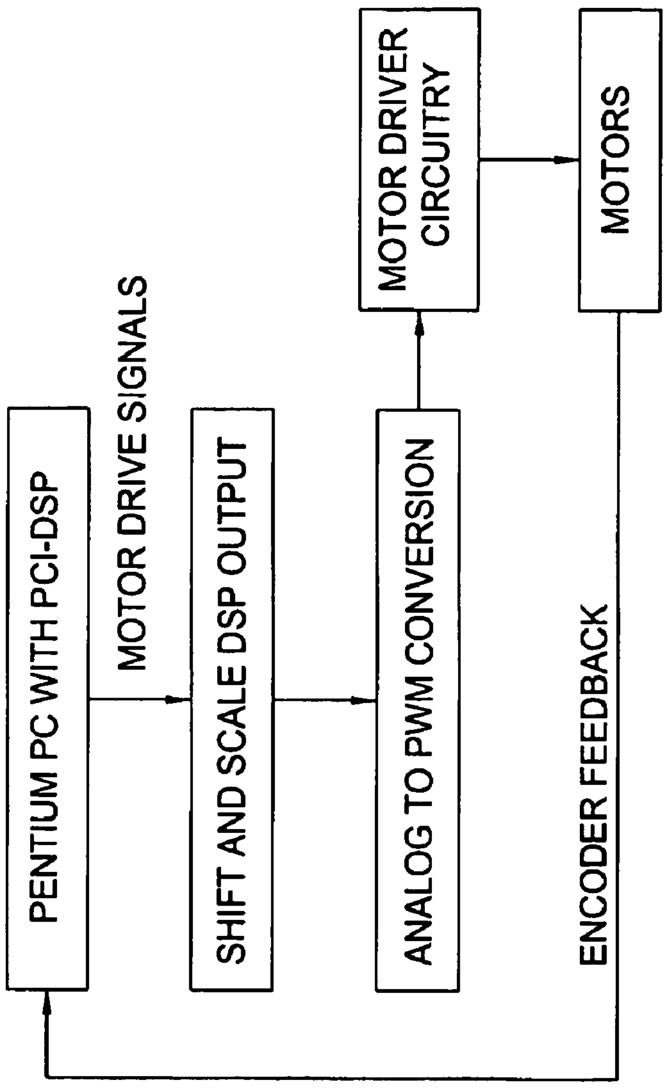
FIG. 18 is a block diagram of the electronics and control system used in one embodiment of the manipulator arm of the present invention.

The electronics and control for the manipulator arm robot consisted of four major sections: PC with a MEI DSP motor driver PCI card, an analog circuit to shift and scale the output voltage from the MEI card, a microcontroller to convert each axis' analog voltage to a PWM signal, and an H-Bridge ICS to drive the motors. A block diagram of the system is shown in FIG. 18. Each hardware section will be described in detail, followed by the PC software controlling the PCI-DSP card and the software running on the micro-controller.

The first section of the hardware was a PC with Motion Engineering, Inc. PCI/DSP motion controller card. This card used an Analog Devices DSP chip running at 20 MHz to provide closed-loop PID control of up to four axes simultaneously. It had encoder inputs for positional feedback. The servo analog outputs were controlled by a 16-bit DAC, which allowed very precise output control. The card also featured several dedicated digital I/O functions, including amplifier enable output, amplifier fault input, home input, positive limit input, and negative limit input. However, only the basic functions were used in this application: servo analog output and digital encoder inputs. The PCI/DSP came with a full-featured C programming library to aid in programming different motion functions. Also provided was a Windows-based program, Motion Control, to configure and tune the controller, as well as to capture data from simple one-axis motion profiles.

Figure 19A:
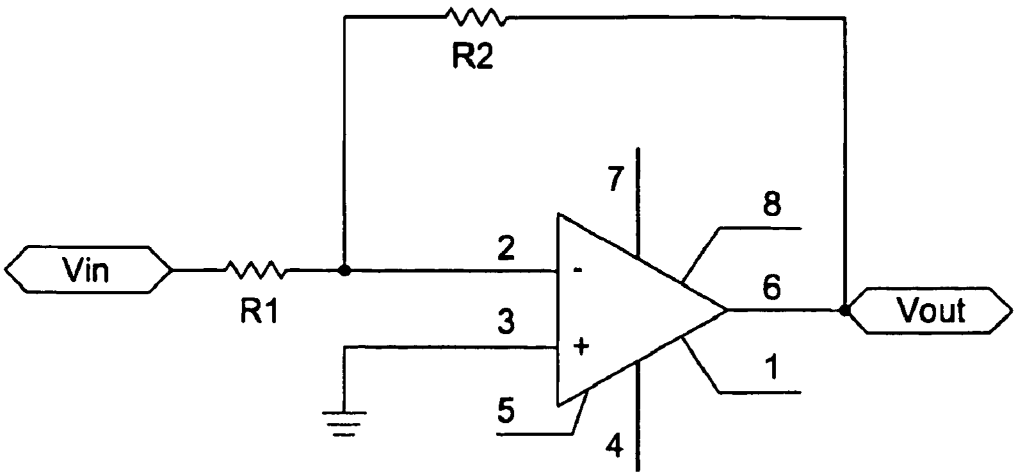
FIG. 19A is an inverting amplifier circuit.

The output from the PCI/DSP was an analog signal with a range of +/−10V. In order to interface with the microcontroller, this signal was converted to a 0.5V range. Two simple op-amp circuits performed this function. Both op-amp circuits used the LM318 op-amp from National Semiconductor. The first section was a standard inverting circuit with a gain of −0.25. This converts the +/−10V input into a −/+2.5V output. This circuit is shown in FIG. 19A. The second section is a summing amplifier circuit with a transfer function given by:

$$V_0 = (V_z - V_1)\frac{R_z}{R_1}$$

Figure 19B:
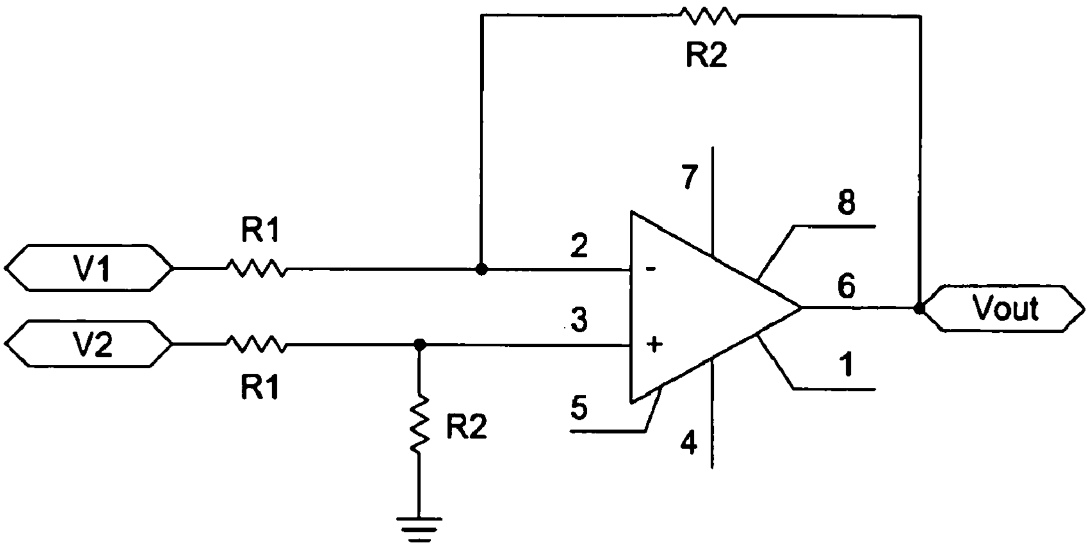
FIG. 19B is a summer amplifier circuit.

With V2 a constant 2.5V, an output voltage of 0–5V results. This circuit is shown in FIG. 19B.

Capacitors were placed at the output of each op-amp to filter out high frequency noise. This two-amplifier circuit is duplicated exactly for each axis. The 2.5V reference is supplied by a 10 K potentiometer.

After the analog voltages were scaled and shifted, each was sampled by the PsoC (Programmable System on a Chip) microcontroller and converted to a PWM output signal and a direction signal. The PsoC also provides direction output based on the input voltage. The PsoC is made by Cypress Semiconductor, and is an 8-bit microcontroller with several generic digital and analog "blocks" that can be configured using the PsoC Designer software package to perform many different functions. These functions include, but are not limited to: ADCs, DACs, PWM generators, timers, UARTS, LCD drivers, filters, and programmable amplifiers. PsoC Designer also provides an API accessible from C and assembly to interface with these on-board components. For the embodiment described here, a single ADC, an analog multiplexer, and three PWM generators were used. The duty cycle of the PWM outputs are directly proportional to the analog input signals. Table 8 summarizes the function of the microcontroller.

TABLE 8

Microcontroller Function

| Analog Input | PWM Positive Duty Cycle | Direction Output |
|---|---|---|
| Vin = 2.5 V | 0% | X |
| 0 < Vin < 2.5 | 50% < Dc < 0% | Low |
| 2.5 < Vin < 5 | 0% < Dc < 50% | High |

The outputs of the microcontroller circuit were fed to the inputs of the FAN8200. These were H-Bridge Driver circuits, in a 20-pin surface mount package. Each driver had an enable and direction input. For this embodiment, the PWM signal was fed to the enable input, and the direction output of the microcontroller was fed to the direction input of the motor driver. The motors on the robot were connected directly to the PCI/DSP card, with no signal conditioning required. As mentioned previously, the PsoC microcontroller sampled each of the three analog outputs, and updated the corresponding PWM duty cycle and direction output accordingly.

Figure 20:
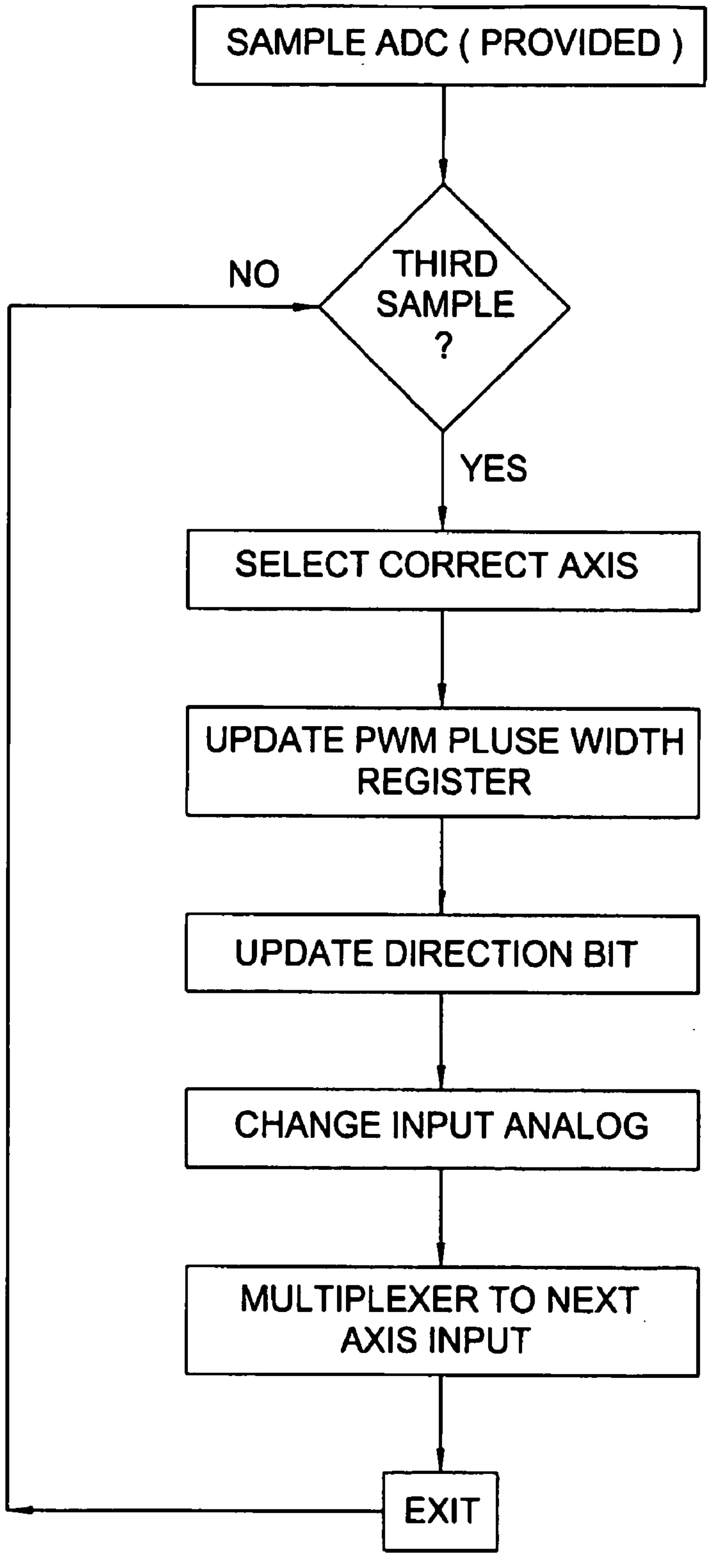
FIG. 20 is a flowchart for an interrupt service routine used in one embodiment of the manipulator arm of the present invention.

The majority of the code was executed in the ADC interrupt service routine. A flowchart of the ISR is shown in FIG. 20. After initialization, the PsoC main program entered an endless loop. The ADC was set up to generate a periodic interrupt. After the data was sampled, a check was performed to see if the last two samples had been ignored. Since three different input signals were sampled, a limitation of the hardware required skipping two samples before getting a valid value. If the last two samples were skipped, the appropriate PWM pulse width register and direction bit were set. Next, the input of the analog multiplexer was switched to the next axis input. This cycle was then repeated when the next interrupt occurred.

The other software element in the system was the PC program that was used for testing the robot. This was a console-based Windows program that used the Motion Engineering library to send commands to the PCI/DSP. This program can move each axis individually, or move all three simultaneously using the DSP's coordinated motion functions, allowing the user to enter a desired position, in encoder counts, for each axis. The DSP card then creates an appropriate motion profile, and moves each motor to the correct position. This program also was used to generate impulse responses for each motor for analysis.

Figure 21:
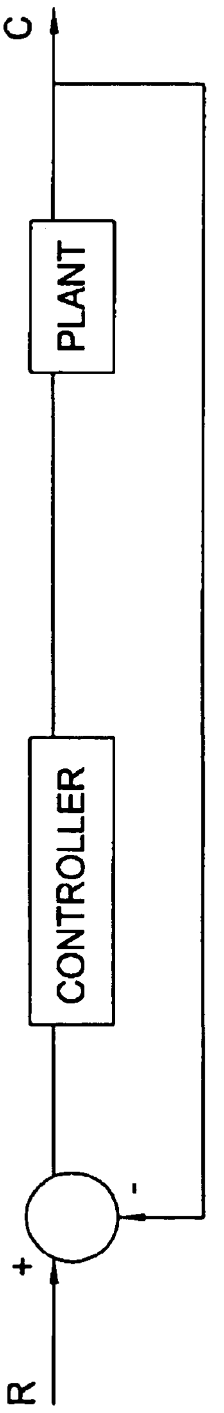
FIG. 21 is a block diagram of a controller and plant for a modern control system for control design of a three-link manipulator arm according to one embodiment of the present invention.

There are several techniques available for designing system controls; here, modern control theory was used for control design of a three link robotic arm. A typical modern control system contains a plant and a controller in the feed forward. This design theory is shown in FIG. 21 as a block diagram. Modern control theory is an effective and commonly used theory for control design.

In this case, modern control theory was used to design three separate controllers. Three controllers were required in order to control the three motors used to manipulate the arm. In order to do this, it was assumed that three separate systems exist. Each system was designed assuming that only one motor, the motor being controlled in the system, was active. This was acceptable based on the method for determining the reaction of a system to a disturbance.

Figure 22:
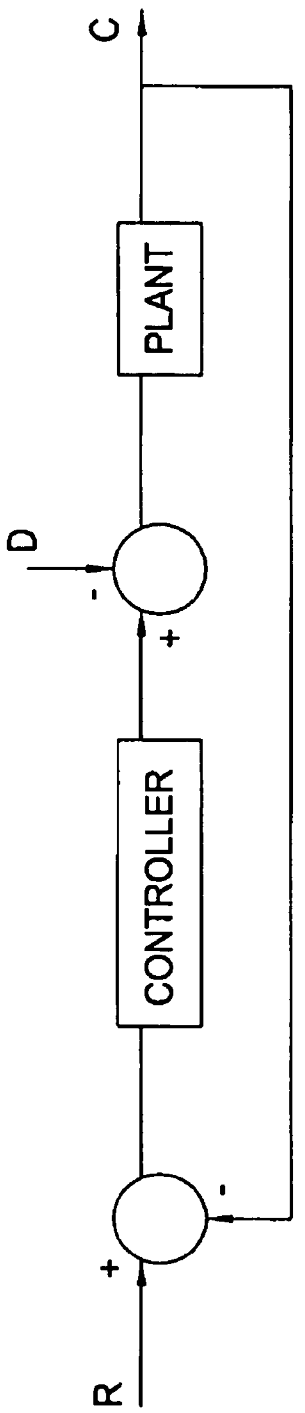
FIG. 22 is a block diagram of a controller and plant for a modern control system for a three-link manipulator arm according to one embodiment of the present invention. In this block, a disturbance is included.

Shown in FIG. 22 is a block diagram of a system that includes a disturbance. In order to determine how the output, C, responds to the input, R, the disturbance, D, is set to zero. Using this method, the uncontrolled motors are considered equivalent to the disturbance and are set to zero. With this, a controller was then designed based on a single output containing a single input. However, three separate systems are still required, since there are three separate outputs. These outputs are motor positions, in encoder counts, of axes 1, 2 and 3.

Figure 23A:
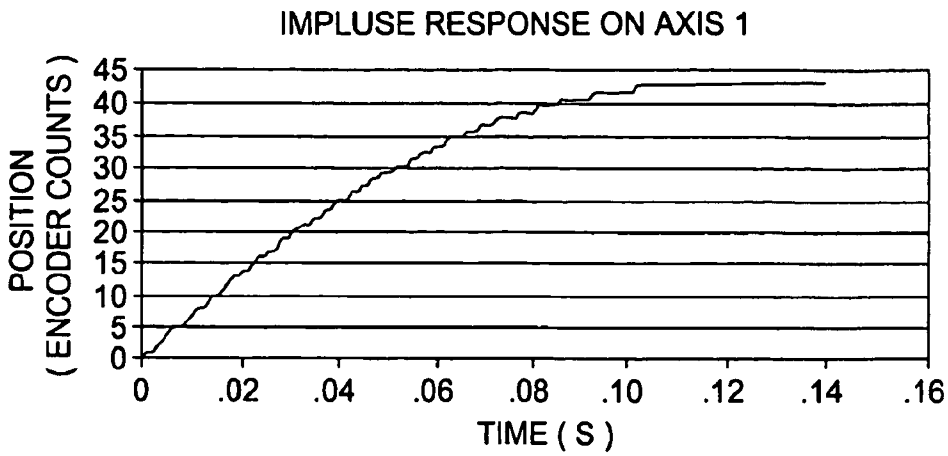
FIGS. 23A–C are plots of motor position, based on encoder counts versus time in seconds, for the three motors used in the linkages of the three-link manipulator arm according to one embodiment of the present invention.
Figure 23B:
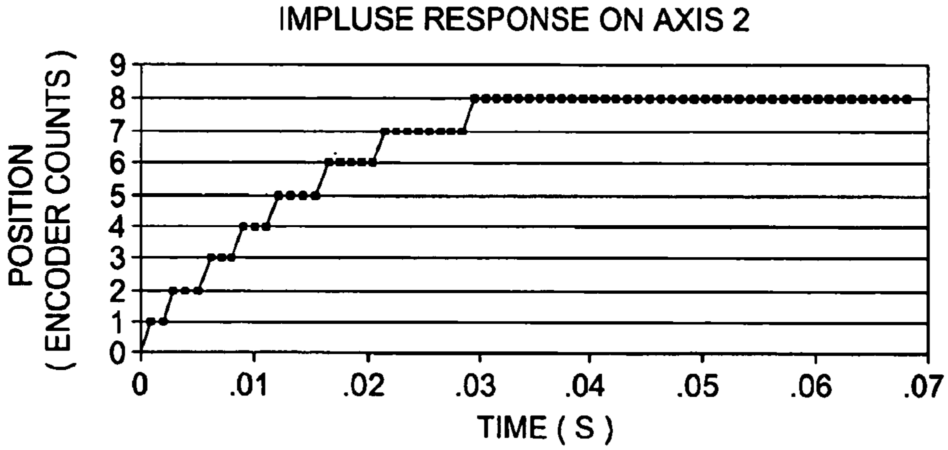
Figure 23C:
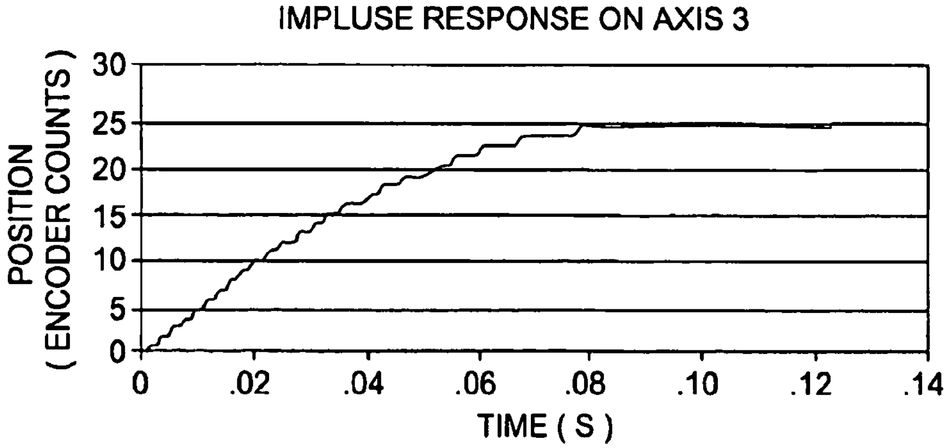

There are several methods a designer can use to design a plant. Most methods used are analytical. In this case an experimental approximation of the plant was created. This was an effective and verifiable method for approximating the system. To collect the experimental data, a computer program was used to send a voltage impulse to the motor. The program simultaneously recorded the position of the motor, using the encoder. This procedure was performed three separate times, once for each motor. The data was then used to construct plots of motor position (based on encoder counts) versus time in seconds. Plots from the data are shown in FIGS. 23A, 23B and 23C. In these plots, axis 1 represents the motor for link 1, axis 2 represents the motor for link 2, and axis 3 represents motor for link 3.

From analyzing the data in FIGS. 23A, 23B and 23C, an approximation of the time response to an impulse input was developed. Experience helped determine that this system most likely contained two more poles than zeros. To determine if this was correct, approximations of the digital systems were made using a continuous time domain. An algorithm for the plant in the continuous time domain was developed for FORTRAN using Maple V. This algorithm was then integrated into an error subroutine. A simplex search program to determine the values of up to 9 variables utilized the error subroutine. The program ran until it could no longer reduce the sum of the square of the error developed by the approximate plant, compared to the experimental plant.

Multiple configurations of the plant were used to find the approximation to the experimental plant. This included the use of complex poles, as well as changing the number of poles and zeros in the transfer function. From these configurations, it was determined that the plant, G(s), can be modeled using the transfer function in the continuous time domain shown the following in equation. In this equation, the poles are 0, −b and −c, and the zero is −α.

$$G(s) = \frac{s+\alpha}{s(s+b)(s+c)}$$

Using the simplex search program, along with the error subroutine, the following system plant values were determined:

System for axis 1:

a=427251.2 b=465.3229 c=18.28435 sum of square of error=16.3779

System for axis 2:

a=$22.219726*10^9$ b=$4.142605*10^{16}$ c=56.9335 sum of square of error=2.86986

System for axis 3:

a=282220.0 b=414.5029 c=24.2966 sum of square of error=9.7724

Since all motors were identical, they should have similar system poles and zeros, even though they are located in different positions on the robot. This was shown to be true for the systems for axis 1 and 3. However, the system for axis 2 did not conform to the other two systems very closely. This was most likely due to poor data. A larger impulse on the motor for axis 2 would have helped to obtain more realistic data.

Figure 24A:
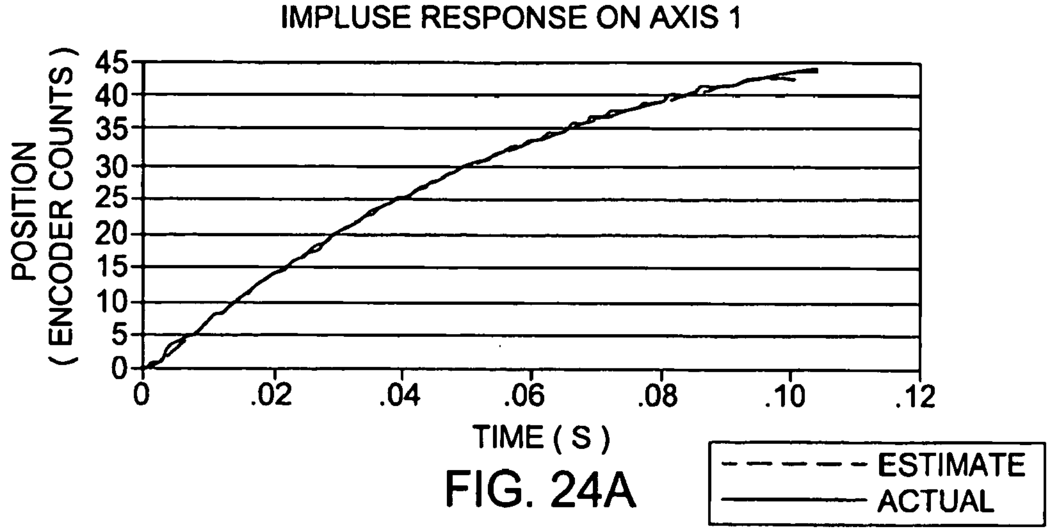
FIGS. 24A–C are plots of motor position, based on encoder counts versus time in seconds, for the three motors used in the linkages of the three-link manipulator arm according to one embodiment of the present invention.
Figure 24B:
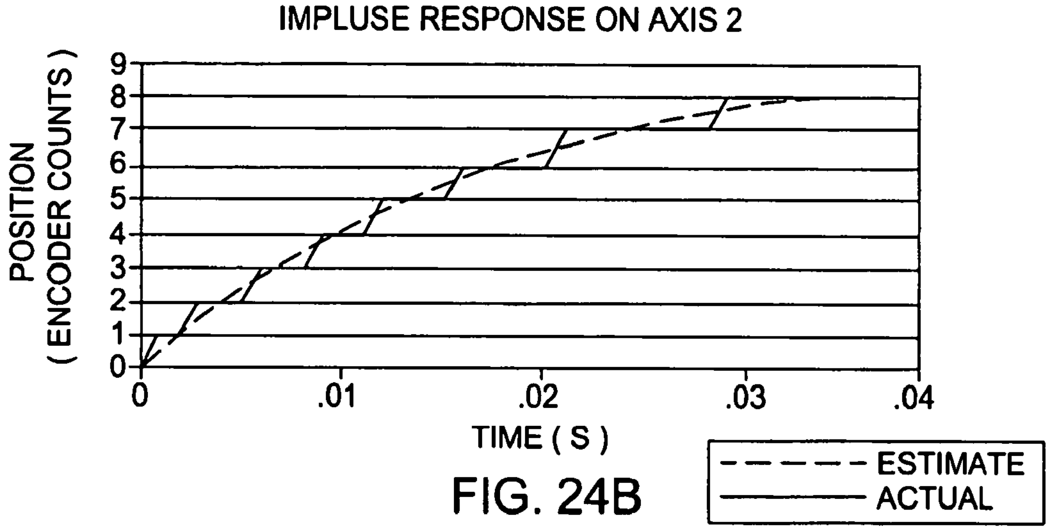
Figure 24C:
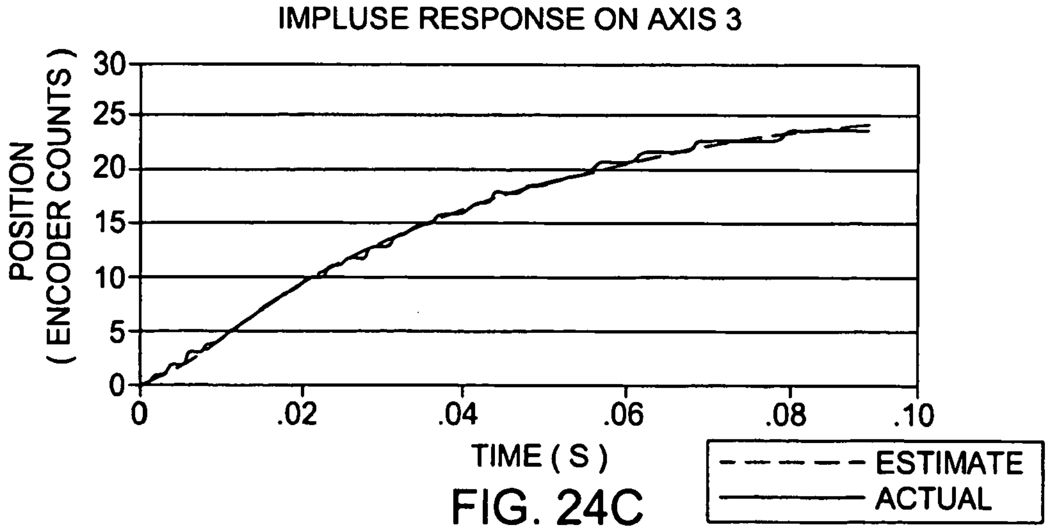

To see how well the system in the continuous time domain reflected the data taken from the digital system, the error subroutine was used once again. This time the error subroutine was compiled as a program rather than as a subroutine. By substituting the above values for a, b and c into the error program, the continuous fit was mapped to the actual digital data. The results were plotted once again as motor position (based on encoder counts) versus time in seconds. These plots are shown in FIGS. 24A, 24B and 24C. As shown in each of these figures, the approximation developed was a good fit to the actual data.

To control the motor positions on the robot, a PID controller was used. When using a PID controller, the controller from FIGS. 19A and 19B takes the form of the following equation.

$$D(s) = K_p + K_D s + \frac{K_1}{s}$$

Where $K_p$ is the proportional constant, $K_D$ is the derivative constant, and $K_1$ is the integral constant. With the PID controller, the system becomes a type 2 system. This means that the error in the response to a step and ramp input is zero. However, the error for the response to a parabolic input is $1/K_a$. Where $K_a$ is the acceleration constant and is defined as:

$$K_a = \lim_{s\to 0}[s^2 D(s)G(s)] = \frac{K_1\alpha}{bc}$$

Since the input can be defined, a parabolic input is not used.

Computing the values for $K_p$, $K_D$ and $K_1$ was done using Routh Analysis along with Ziegler-Nichols tuning. Routh Analysis uses the characteristic equation of the system transfer function. In this case, though, $D(s)=K_p$, only. The transfer function of this system with gain only, using G(s) as defined above, is shown in the following equation.

$$TF = \frac{K_p(s+\alpha)}{S^3 + (b+c)s^2 + (bc+K_p)s + \alpha K_p}$$

Note that Routh Analysis only can be used if the system for D(s)=1 is stable. This is true if the characteristic equation of the system when D(s)=1 has stable roots. Stable system poles, or roots of the characteristic equation, are roots that have negative real values or are located at the origin. The following equation is the characteristic equation for the system when D(s)=1.

$$CE = s\,(s+b)\,(s+c)+(s+\alpha)$$

The following poles or roots of CE are:

System for axis 1:
- −467.3563980,
- −8.125425989−29.12326516*I,
- −8.125425989+29.12326516*I System for axis 2:
- −4142605000e17,
- −56.93350000,
- −1811514786e−12

System for axis 3:
- −417.1080124,
- −10.84574379−30.11125593*I,
- −10.84574379+30.11125593I Since all poles have negative real parts, the uncontrolled system was stable and Routh Analysis can be used.

Using the characteristic equation, or the denominator from the equation, solving for TF, above, Routh Analysis is performed as follows:

| | |
|---|---|
| $s^3$ | $a_0 a_2$ |
| $s^2$ | $a_1 a_3$ |
| $s^1$ | $b_1$ |
| $s^0$ | $c_1$ |

where:

$$a_0 = 1$$

$$a_1 = (b+c)$$

$$a_2 = (bc+K_p)$$

$$a_3 = \alpha K_p$$

$$b_1 = \frac{a_1 a_2 - a_0 a_3}{a_1}$$

$$c_1 = \frac{b_1 a_3 - a_1 * 0}{b_1} = a_3$$

Using Maple V, the term ($b_1$*s) is set equal to zero and then solved for $K_p=K_{p(max)}$. The results are as follows:

System for axis 1:
$K_{p(max)}$.=9.641293894

System for axis 2:
$K_{p(max)}$.=$0.4409880606*10^{16}$

System for axis 3:
$K_{p(max)}$.=15.68292936

These results were all obtained using Maple V.

In order to use Ziegler-Nichols tuning with Routh Analysis, the system period was also needed. The system period was found by setting $s=j\omega$, $K_p=K_{p(max)}$, and solving for $\omega$ (system frequency in rad/s) from the following equation.

$$\alpha_1(j\omega)^2+\alpha_3=0$$

Since, $$\omega=2\pi f.$$

Then the system period in seconds was:

$$T = \frac{1}{f} = \frac{2\pi}{\omega}$$

The resulting system periods were as follows:

System for axis 1:
T=0.06807959499 sec

System for axis 2:
T=$0.4087460141*10^{-8}$ sec

System for axis 3:
T=0.06256709734 sec

With the Ziegler-Nichols tuning equations for $K_p$, $K_1$, and $K_D$, the controller, D(s), as defined above, was designed. The Ziegler-Nichols tuning equations for PID control are shown below.

$$K_p = 0.6K_{p(\max)}$$

$$K_1 \le \frac{2K_p}{T}$$

$$K_D \ge \frac{K_p T}{8}$$

The resulting values for $K_p$, $K_1$, and $K_D$ are as follows:

System for axis 1:
$K_p$=5.784776336
$K_D$=0.04922815376
$K_1$=169.9

System for axis 2:
$K_p$=0.2645928364e16
$K_D$=1351890.840
$K_1$=0.1294656473e25

System for axis 3:
$K_p$=9.408
$K_D$=0.07357890648
$K_1$=300.7331456

Figure 25:
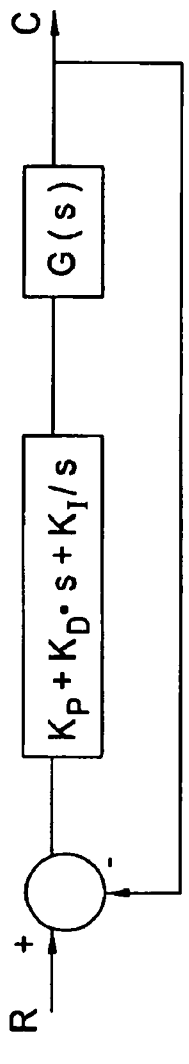
FIG. 25 is a system block diagram for a controller based on Ziegler-Nichols tuning.

The resulting system with PID control for all systems is shown in FIG. 25, where G(s), $K_p$, $K_D$, and $K_1$, are previously defined constants and functions, C is the motor position in encoder counts and R is the input position, in encoder counts.

Figure 26A:
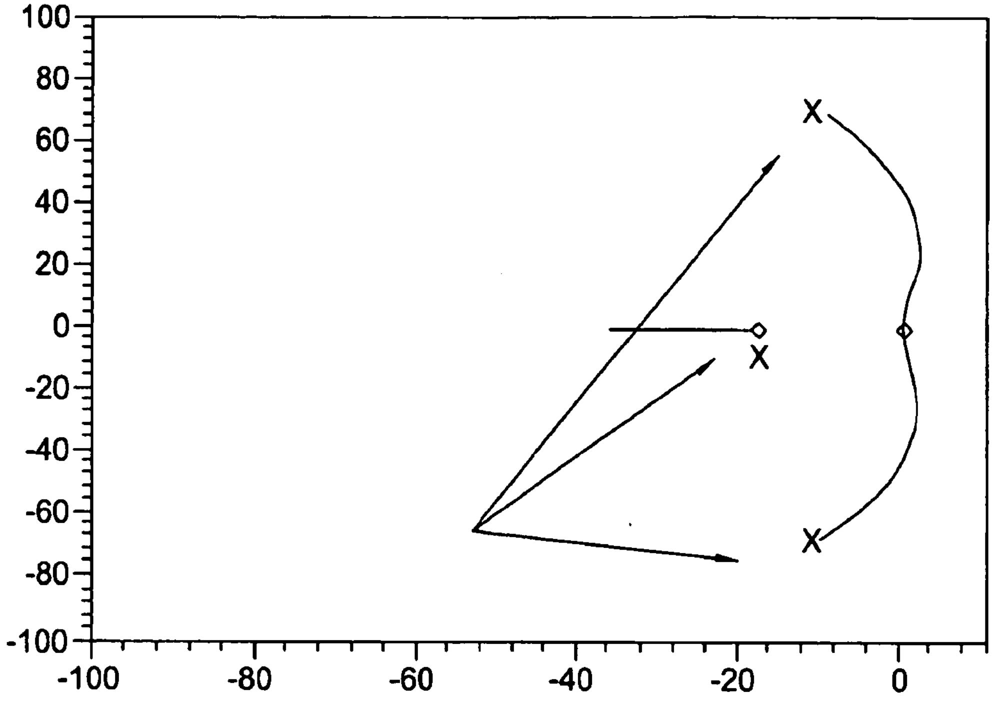
FIGS. 26A and B show plots of the root locus for links 1 and 3.
Figure 26B:
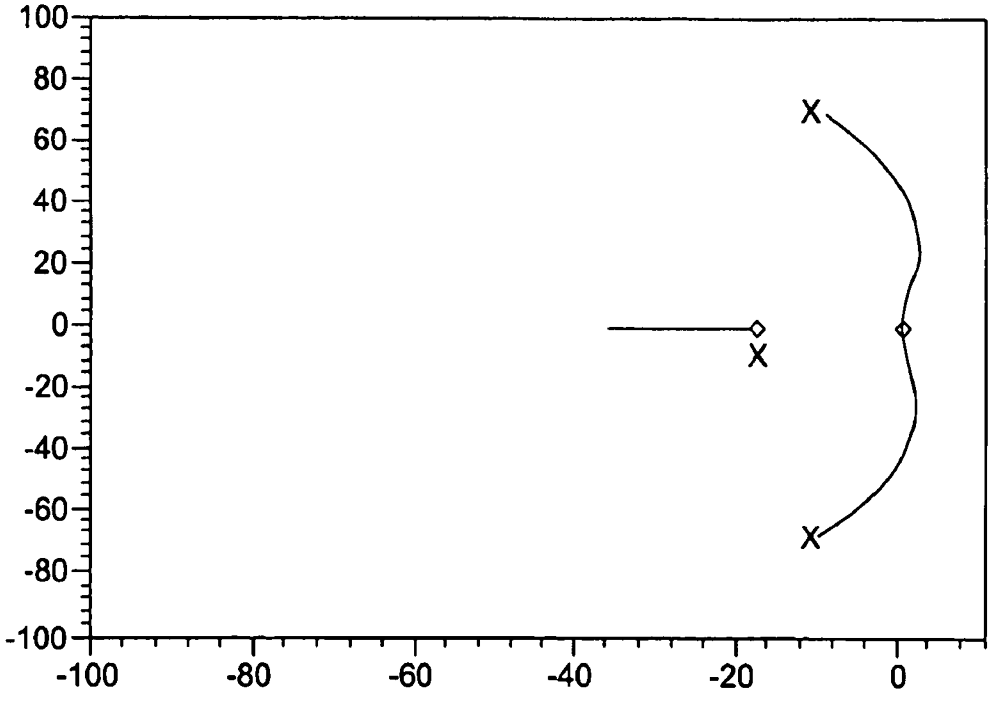
FIG. 26B shows the results for link 3.

One way to decide if these PID values were reasonable was to do a root locus plot of the open loop transfer function, D(s)*G(s). System stability also could be found from the root locus plot. That is, the poles or roots of the characteristic equation on the root locus should be located in the negative real plane. These plots, shown in FIGS. 26A and 26B are made using a Maple V program. Note that the root locus for axis 2 is not shown. From viewing the previous results for determining the PID control values, it was obvious that the data for axis 2 does not follow the data for axes 1 and 3 as would be expected.

Figure 27A:
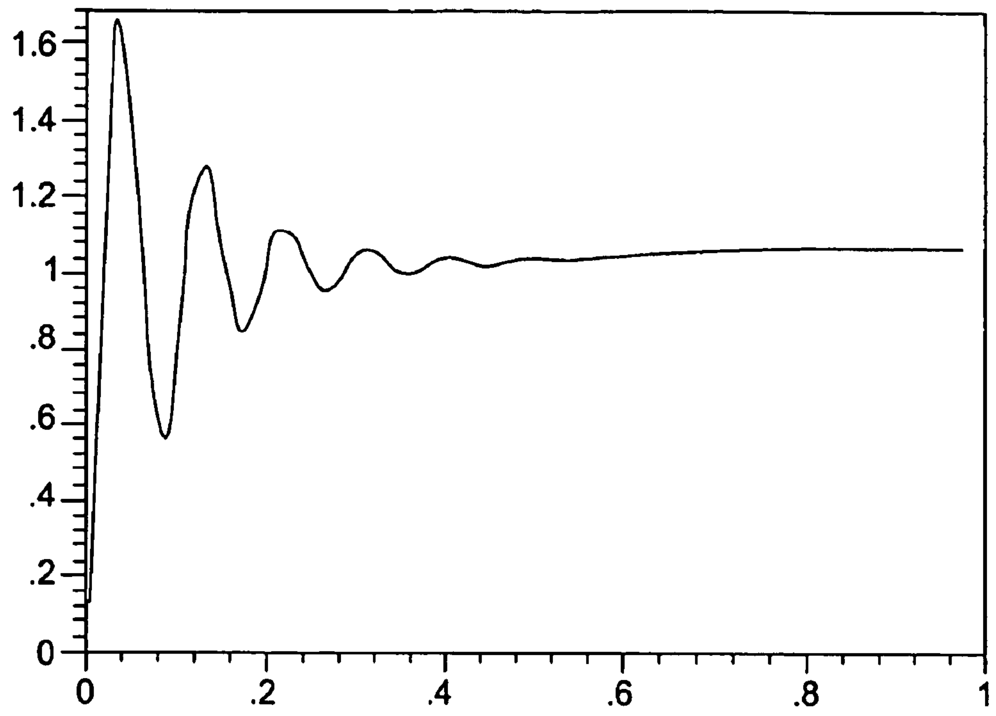
FIGS. 27A–C show plots of time response to unit input of a three-link manipulator arm according to one embodiment of the present invention.
Figure 27B:
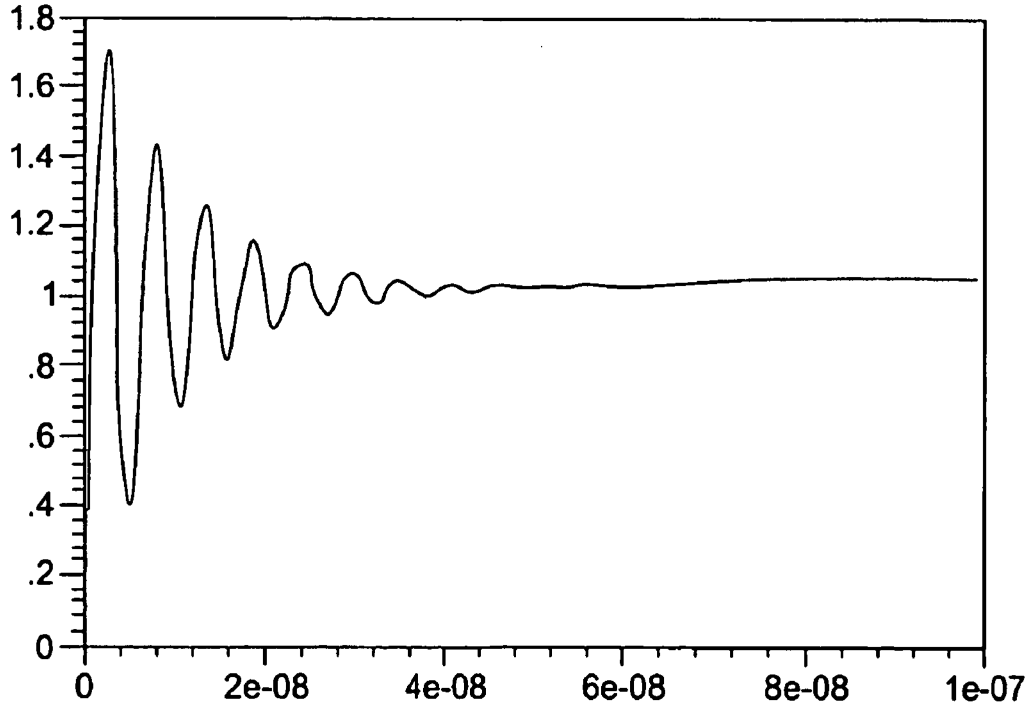
Figure 27C:
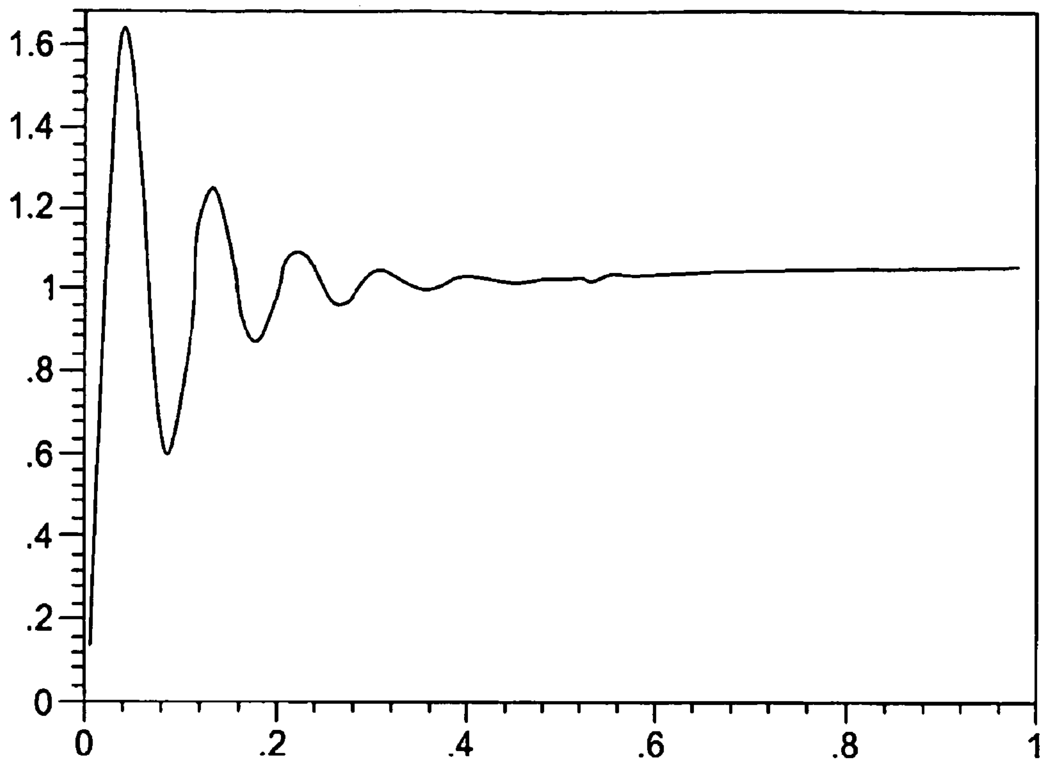

As shown in FIGS. 27A and 27B, both systems for axes 1 and 3 were stable, as was the system for axis 2. When looking at FIGS. 26A and B, complete optimization of the system would align the three poles. Since all systems were stable, a time response to a unit input into the system was analyzed. Once again, the Maple V program was used to determine the responses shown in FIGS. 27A, 27B and 27C. In FIGS. 27A, 27B and 27C, the abscissa is time in seconds, and the ordinate is motor position in encoder counts.

All responses shown in FIGS. 27A through C were stable responses. However, in each case, there was over 66 percent overshoot, and such overshoot is undesirable for control of the robotic arm. By using a lead-lag compensator, the overshoot was greatly reduced.

Adjusting the phase margin of a system through the use of a lead or a lead-lag compensator is a technique that generally reduces the percent overshoot of a system. The phase margin is the angle between the negative abscissa and the point on the Nyquist diagram of the system, where the magnitude is 1. In most cases, a phase margin of about 60 degrees is optimal for reducing percent overshoot.

From using a Nyquist plot program, the following data was obtained.

System for axis 1:

Phase Margin=180−162.9633=17.84 degrees $\omega_c$=71.999 rad/s

G(jω)=1.0007~1.0

$\Phi_{(added)}$=60−17.84=42.96 degrees

To compensate for phase loss due to the lag compensator:

$\Phi_{(added)}$=45.0 degrees

System for axis 3:

Phase Margin=180−161.90512=18.095 degrees $\omega_c$=71.999 rad/s

G(jω)=1.0007~1.0

$\Phi_{(added)}$=60−18.095=41.905 degrees

To compensate for phase loss due to the lag compensator:

$\Phi_{(added)}$=48.0 degrees

There are a few things to note. Once again, the data for axis 2 resulted in compensator design for axes 1 and 3 only. Also, $\omega_c$ may be changed to any desired frequency. G(jω), and $\Phi_{(added)}$ would subsequently change depending on the phase and magnitude at the selected $\omega_c$. However, the phase margin would remain the same.

The following equations were used to define a lead and lag compensator, respectively.

$$\frac{1}{k} = \left[\tan\left(\frac{\phi_{added}+90}{2}\right)\right]^2$$

$$\sqrt{k1} = \omega_c$$

$$\text{lead} = \frac{1}{k}\frac{(s+k)}{(s+1)}$$

$$\frac{n}{m} = \frac{1}{G(j\omega)\sqrt{\frac{1}{k}}}$$

$$M = \frac{\omega_c}{5}$$

-continued $$\text{Lag} = \frac{n}{m}\frac{(s+m)}{(s+n)}$$

The resulting compensators from equations 11 and 12 for systems for axes 1 and 3 were as follows:

Compensator for axis 1:

$$\text{lead} = \frac{173.82096}{29.82296}\frac{(s+29.82296)}{(s+173.82096)}$$

$$\text{lag} = \frac{5.96459}{14.3998}\frac{(s+14.3998)}{(s+5.96459)}$$

Compensator for axis 3:

$$\text{lead} = \frac{203.9772}{30.0563}\frac{(s+30.0563)}{(s+203.9772)}$$

$$\text{lag} = \frac{6.0071}{15.65988}\frac{(s+15.65988)}{(s+6.0071)}$$

Figure 28:
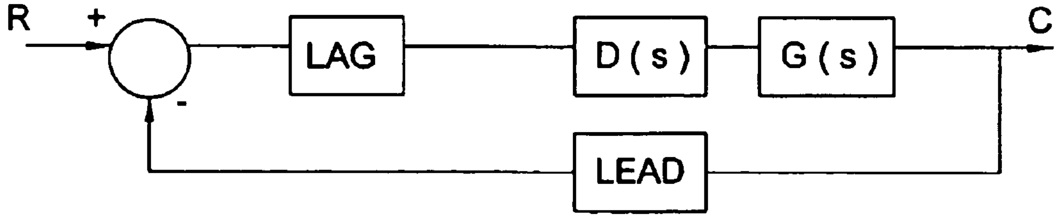
FIG. 28 is a system block diagram for a controller with lead and lag compensators integrated into the design.

The lead and lag compensators are integrated into the design as shown in FIG. 28.

Since zeros placed closer to the origin than poles create overshoot, the lead compensator was placed in the feedback. This is because if placed in the feed forward, a zero would be located between the origin and a pole in the root locus plot. For this same reason, the lag compensator was placed in the feed forward.

The effect of these compensators on the system was analyzed. First, the Nyquist plot program, was used once again. This was done to see what effect the compensators had on the phase margin. Finally, a plot of the response of the systems to a unit step input was made using the Maple V program 1.

Resulting data from the Nyquist plot program:

System for axis 1:

Phase Margin=180−123.88=56.12 degrees@ω=73.199 rad/s

System for axis 3:

Phase Margin=180−120.238=59.76 degrees@ωc=79.599 rad/s

Figure 29A:
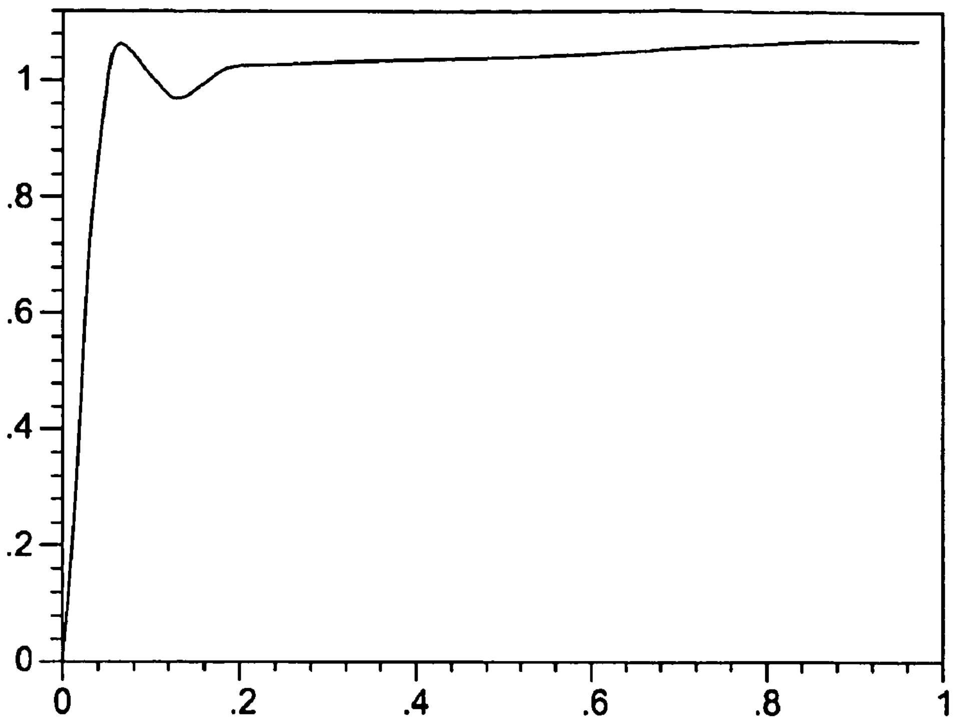
FIG. 29A shows the results for link 1 and FIG. 29B shows the results for link 3.
Figure 29B:
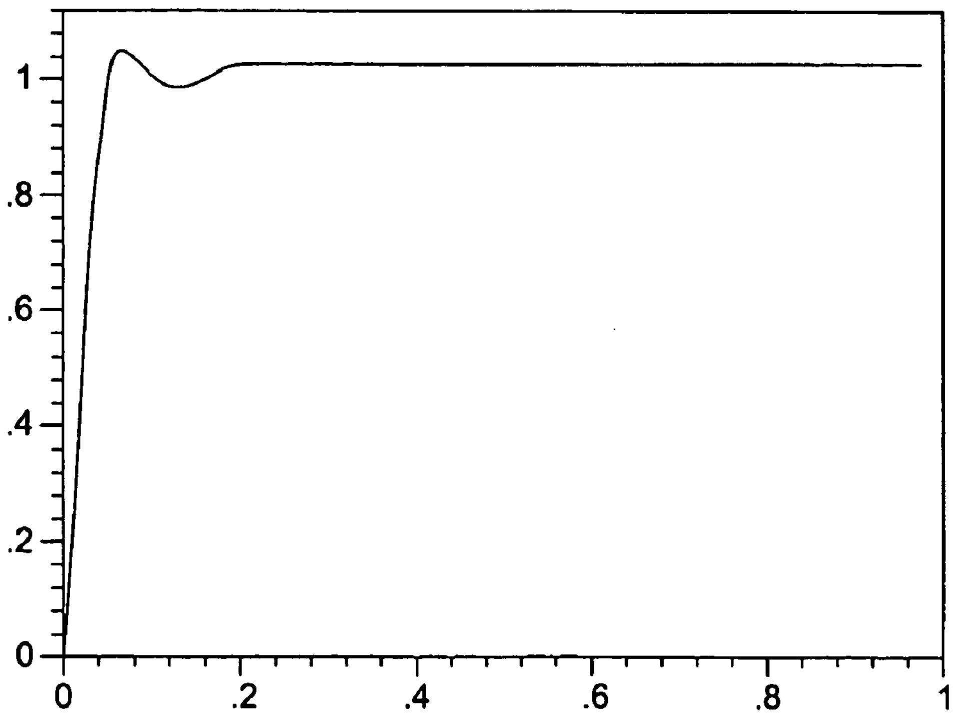

This was proof that the compensator design was successful in adjusting the phase margin to the desired 60 degrees of phase. Shown in FIGS. 29A and 29B are the responses of the systems for axes 1 and 3 after the addition of the compensators. These plots were made using the Maple V program. Again, the abscissa is time in seconds and the ordinate is motor position in encoder counts.

As shown in FIGS. 29A and 29B, the compensators greatly reduced the percent overshoot. The percent overshoot was reduced to a mere only about 4 percent, a great improvement over the 66 percent figure.

Once the controller design was complete in the continuous time domain, it could be converted to the discrete time domain. This is required in order to control a digital system. However, it was only necessary to convert the compensators and controller to the discrete time domain. When this was done, a control algorithm was introduced to the computer program.

To convert the compensators and controllers to the discrete time domain or z-domain, Tustin's method was used.

Tustin's method is only good for linear systems and introduces the relationship shown in the following equation.

$$s = \frac{2}{T}\frac{(z-1)}{(z+1)}$$

where T represents the sampling period of the controller. Substituting this equation into the controller, lead compensator, and lag compensator yields the following equations.

$$D(z) = K_p + \frac{2K_D(z-1)}{T(z+1)} + \frac{K_1 T(z+1)}{2(z-1)}$$

$$\text{Lead} = \frac{(2z - 2 + kTz + kT)1}{(2z - 2 + 1Tz + 1T)k}$$

$$\text{Lag} = \frac{(2z - 2 + mTz + mT)n}{(2z - 2 + nTz + nT)m}$$

Figure 30:
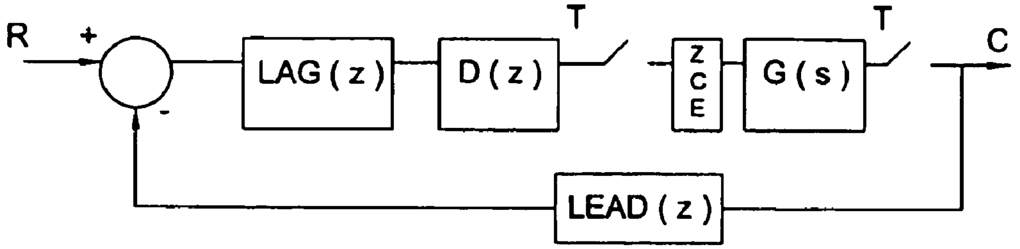
FIG. 30 is a system block diagram for a final design of a controller of a three-link manipulator arm according to one embodiment of the present invention.

The final system block diagram is shown in FIG. 30.

In FIG. 30, the zero order hold of G(s) yields G(z). The conversion of G(s) to G(z) is only made if a model of TF(z)=C(z)/R(z) is made.

Figure 31:
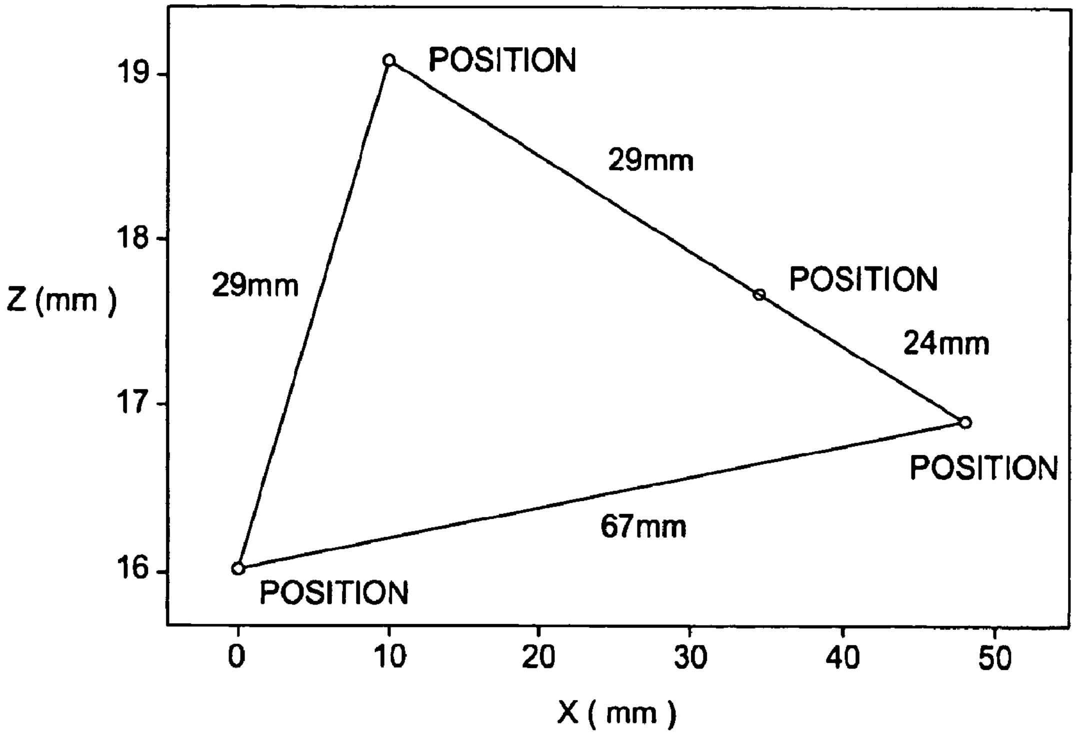
FIG. 31 is the actual movement in the x-z plane of the tip of a three-link manipulator arm according to one embodiment of the present invention.

After the designed components were assembled, a test was performed to verify the controllability and accuracy of the manipulator. The tip of the manipulator, which was attached to a camera, is supposed to move through four points along the sides of the triangle shown FIG. 31, where position 1 is the starting point and ending point, and distance 1,2 is 39 mm, distance 2,3 is 24 mm, distance 3,4 is 67 mm and distance 4,5 is 29 mm.

To test the accuracy of the movement of the tip, the assumed motor rotation angles were input into the controlling program. These input angles controlled the tip movement along the edges of the triangle. Table 9 shows the motor rotation angles, in encoder counts, for four different points. The ratio of encoder counts per degree was 28.9.

TABLE 9

| | Position of tip in encoder counts | | | | |
|---|---|---|---|---|---|
| Axis | Position 1 | Position 2 | Position 3 | Position 4 | Position 5 |
| 1 | −2250 | −1500 | −1250 | −2600 | −2250 |
| 2 | 360 | 200 | 375 | −75 | 360 |
| 3 | 610 | 1400 | 1450 | 2000 | 610 |

The next step was to use the Jacobian to transfer the encoder counts to the xyz coordinates:

$$z = L_1 + L_2\cdot\cos\left(\frac{2\cdot\pi\cdot t_1}{28.9\cdot 360°}\right) + L_3\cdot\cos\left(\frac{2\cdot\pi\cdot t_2}{28.9\cdot 360°} + \frac{2\cdot\pi\cdot t_3}{28.9\cdot 360°}\right)$$

$$x = -\left[L_2\cdot\sin\left(\frac{2\cdot\pi\cdot t_2}{28.9\cdot 360°}\right) + L_3\cdot\sin\left(\frac{2\cdot\pi\cdot t_2}{28.9\cdot 360°} + \frac{2\cdot\pi\cdot t_3}{28.9\cdot 360°}\right)\right]\cdot\cos\left(\frac{2\cdot\pi\cdot t_1}{28.9\cdot 360°}\right)$$

$$z = -\left[L_2\cdot\sin\left(\frac{2\cdot\pi\cdot t_2}{28.9\cdot 360°}\right) + L_3\cdot\sin\left(\frac{2\cdot\pi\cdot t_2}{28.9\cdot 360°} + \frac{2\cdot\pi\cdot t_3}{28.9\cdot 360°}\right)\right]\cdot\sin\left(\frac{2\cdot\pi\cdot t_1}{28.9\cdot 360°}\right)$$

$L_1$=83 mm, $L_2$=$L_3$=59.5 mm, and $t_1$, $t_2$, $t_3$ represent the motor angles in encoder counts of axes 1, 2 and 3.

Shown below in Table 10 are the results of x, y and z coordinates for the four different points.

TABLE 10

| | Position of tip in x, y coordinates | | | | |
|---|---|---|---|---|---|
| | Position 1 | Position 2 | Position 3 | Position 4 | Position 1 |
| X | 9.62 | 34.6 | 48.4 | 0.03 | 9.62 |
| Y | 44.7 | 44.16 | 45.52 | 51.916 | 44.7 |
| Z | 190.67 | 175.9 | 167.8 | 166.1 | 190.67 |

The distance between the four points was then calculated by using the equation shown:

$$Dist=\sqrt{(x_1-x_2)^2+(y_1-y_2)^2+(z_1-z_2)^2}$$

Figure 32:
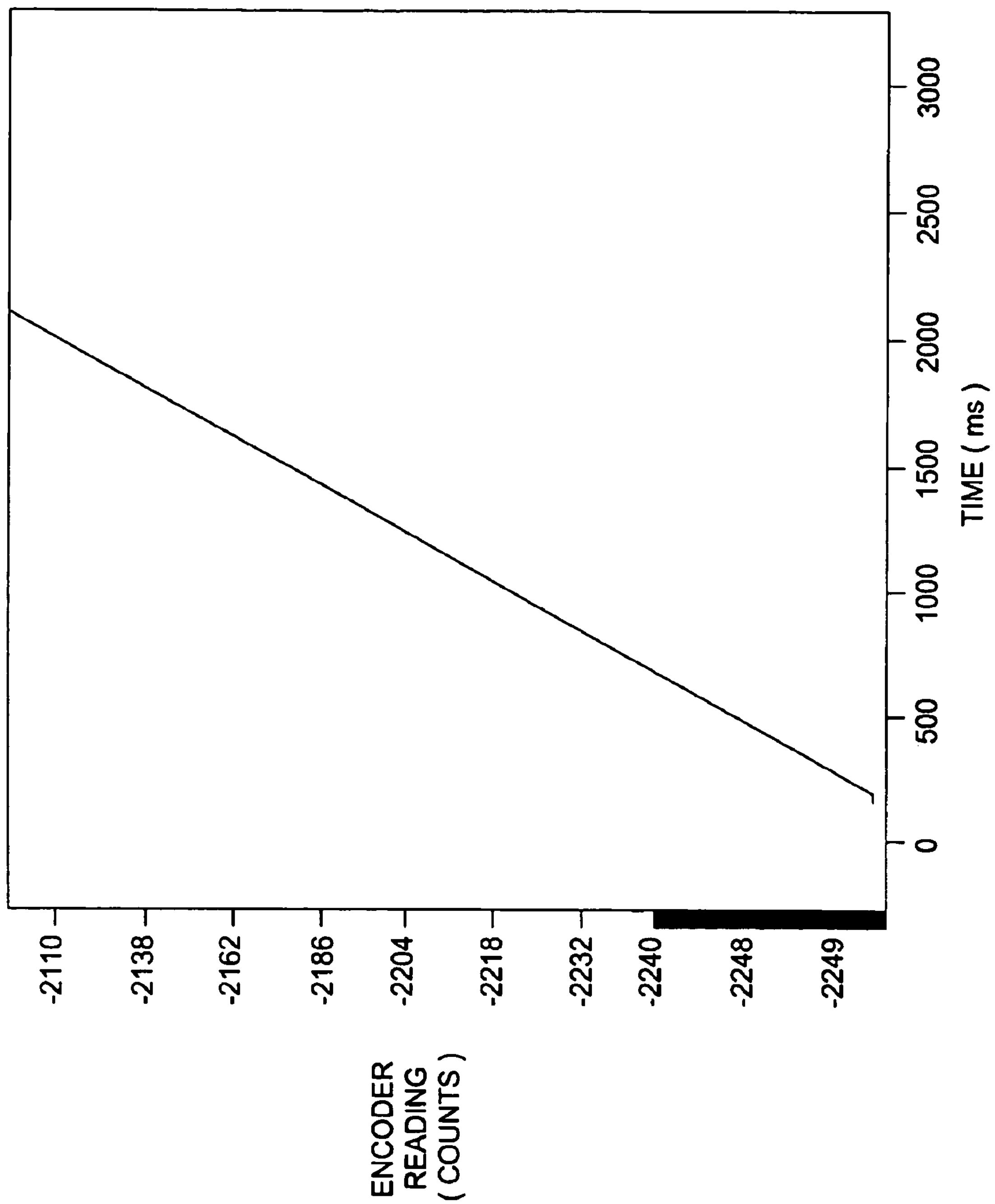
FIG. 32 is a plot of encoder counts versus time showing that movement of the manipulator is linear with time and that the velocity of the tip is constant.

The actual encoder reading was found to describe the movement of the manipulator tip. Shown below in Table 11 are the distances between the four points. FIG. 32 shows that the movement of the manipulator is linear according to time, meaning the velocity of the tip is constant.

TABLE 11

| | Distance between points | | | |
|---|---|---|---|---|
| | pos 1–pos 2 | pos 2–pos 3 | pos 3–pos 4 | pos 4–pos 1 |
| Measured displacement | 39 mm | 24 mm | 67 mm | 29 mm |
| Calculated Displacement | 29 mm | 16 mm | 48 mm | 27.4 mm |
| Error | 25.64% | 33.3% | 28.36% | 5.5% |

The difference between the measured displacement and calculated displacement indicates there is a big error between the two. This was due to several error sources, in the measurement of link lengths $L_1$, $L_2$ and $L_3$, and due to the estimated ratio of the encoder counts to degrees. A source of mechanical error is backlash at the gear mesh.

While the present invention has been described with reference to specific embodiments, it should be understood by those skilled in the art that various changes may be made and equivalents may be substituted without departing from the true spirit and scope of the invention. In addition, many modifications may be made to adapt a particular situation, material, or process to the objective, spirit and scope of the present invention. All such modifications are intended to be within the scope of the invention.

What is claimed is:

1. A mobile robot comprising:

(a) a body sized to operate within a cavity of an animal;

(b) a translational mobility component coupled with the body;

(c) a motor coupled with the translational mobility component;

(d) a power supply coupled with the motor;

(e) a controller component coupled with the body; wherein the robot is configured to apply translational pressure on any a surface for purpose of mobility or immobility.

2. The robot of claim 1, wherein the mobility component comprises at least one wheel.

3. The robot of claim 1, wherein the mobility component comprises a first wheel and a second wheel, wherein the first and second wheels are configured to rotate independently of each other.

4. The robot of claim 1, wherein the body has a substantially cylindrical shape.

5. The robot of claim 1, wherein the body is shaped substantially like a cylinder, sphere, snake, or small vehicle.

6. The robot of claim 1, wherein the robot is configured to travel forward and backward along a path that is perpendicular to the length of the body.

7. The robot of claim 1, wherein the controller is wirelessly coupled with the motor.

8. The robot of claim 1, wherein the controller comprises a wireless transmitter and wherein the robot further comprises a wireless receiver.

9. The robot of claim 1, wherein the controller is physically coupled with the motor.

10. The robot of claim 1, wherein the cavity is an abdominal cavity.

11. The robot of claim 1, wherein the cavity is a peritoneal cavity.

12. The robot of claim 10, wherein the peritoneal cavity has been insufflated with a gas.

13. The robot of claim 1, wherein the at least one surgical component comprises a manipulator device.

14. The robot of claim 1, wherein the at least one surgical component comprises a sensor device.

15. The robot of claim 1, wherein the at least one surgical component comprises a manipulator device and a sensor device.

16. A mobile robot comprising:

(a) a body sized to operate within a cavity of an animal, the body comprising a single axle;

(b) first and second mobility components coupled to the single axle, the first and second mobility components configures for translational movement;

(c) at least one motor coupled with the first and second mobility components;

(d) a power supply coupled with the at least one motor;

(e) a controller component coupled with the at least one motor; and (f) at least one surgical component coupled with the body.

17. The robot of claim 16, wherein the at least one motor is configured to independently propel each of the first and second mobility components, whereby the body can be steered.

18. The robot of claim 16, wherein the robot is capable of changing direction with a zero radius turn.

19. The robot of claim 16, wherein the robot is configured to apply translational pressure on a surface for purpose of mobility or immobility.

20. The robot of claim 16, wherein the cavity is an abdominal cavity.

21. The robot of claim 16, wherein the cavity is a peritoneal cavity.

* * * * *

UNITED STATES PATENT AND TRADEMARK OFFICE

CERTIFICATE OF CORRECTION

PATENT NO. : 7,199,545 B2

APPLICATION NO. : 11/398174

DATED : April 3, 2007

INVENTOR(S) : Dmitry Oleynikov et al.

It is certified that error appears in the above-identified patent and that said Letters Patent is hereby corrected as shown below:

On The Title Page (56) U.S. Patent Documents
Page 2

Delete the reference "2003/0045888 A1" and replace it with --2002/0045888 A1--

Column 34

Line 58, delete the word "body" and replace it with --motor; and--

Column 36

Line 6, delete the word "configures" and replace it with --configured--

Signed and Sealed this

Second Day of October, 2007

JON W. DUDAS

*Director of the United States Patent and Trademark Office*

UNITED STATES PATENT AND TRADEMARK OFFICE

CERTIFICATE OF CORRECTION

PATENT NO. : 7,199,545 B2
APPLICATION NO. : 11/398174
DATED : April 3, 2007
INVENTOR(S) : Dmitry Oleynikov et al.

It is certified that error appears in the above-identified patent and that said Letters Patent is hereby corrected as shown below:

Column 34

Line 59-61, delete “wherein the robot is configured to apply translational pressure on any a surface for purpose of mobility or immobility” and replace it with -- (f) “at least one surgical component, wherein the robot is configured to apply translational pressure on any surface for purposes of mobility or immobility.” --

Signed and Sealed this

Eighth Day of January, 2008

JON W. DUDAS

*Director of the United States Patent and Trademark Office*